US010500337B2

(12) United States Patent
Fabien et al.

(10) Patent No.: US 10,500,337 B2
(45) Date of Patent: Dec. 10, 2019

(54) AUTO-INJECTOR

(71) Applicant: APTAR FRANCE SAS, Le Neubourg (FR)

(72) Inventors: David Fabien, Plouarzel (FR); Thomas Gomez, Saint Aubin de Medoc (FR); Anthony Saussaye, Louviers (FR); Philippe Pinheiro, Incarville (FR)

(73) Assignee: APTAR FRANCE SAS, Le Neubourg (FR)

( * ) Notice: Subject to any disclaimer, the term of this patent is extended or adjusted under 35 U.S.C. 154(b) by 102 days.

(21) Appl. No.: 15/575,881

(22) PCT Filed: Jun. 2, 2016

(86) PCT No.: PCT/FR2016/051312
§ 371 (c)(1),
(2) Date: Nov. 21, 2017

(87) PCT Pub. No.: WO2016/193622
PCT Pub. Date: Dec. 8, 2016

(65) Prior Publication Data
US 2018/0207363 A1    Jul. 26, 2018

(30) Foreign Application Priority Data
Jun. 5, 2015   (FR) ...................................... 15 55166

(51) Int. Cl.
*A61M 5/20* (2006.01)
*A61M 5/31* (2006.01)
(Continued)

(52) U.S. Cl.
CPC .............. *A61M 5/20* (2013.01); *A61M 5/31* (2013.01); *A61M 5/315* (2013.01); *A61M 5/32* (2013.01);
(Continued)

(58) Field of Classification Search
CPC .... A61M 2005/206; A61M 5/20; A61M 5/31; A61M 5/3146; A61M 5/315; A61M 5/32; A61M 5/3287
See application file for complete search history.

(56) References Cited

U.S. PATENT DOCUMENTS

2013/0317435 A1* 11/2013 Fabien ................ A61M 5/2033
604/135

FOREIGN PATENT DOCUMENTS

| WO | 2011/109205 A2 | 9/2011 |
|----|----------------|--------|
| WO | 2012/022810 A2 | 2/2012 |

(Continued)

OTHER PUBLICATIONS

International Preliminary Report on Patentability dated Dec. 21, 2017 from the International Bureau in counterpart International application No. PCT/FR2016/051312.
(Continued)

*Primary Examiner* — Brandy S Lee
(74) *Attorney, Agent, or Firm* — Sughrue Mion, PLLC

(57) ABSTRACT

An autoinjector having a body (1) receiving a reservoir (S) containing fluid and including a piston (P), such as a pre-filled syringe; a piston rod (5) that co-operates with the piston (P), the piston rod (5) being movable by an injection spring (8) between a primed position and an injection position in which the piston rod (5) has moved the piston (P) of the reservoir (S) so as to inject the fluid into an injection site; and an indicator device for indicating to the user that the autoinjector may be removed from said injection site. The autoinjector also includes a retarding system to delay the end of actuating the indicator device relative to the end of injection, the indicator device generating a noise while being actuated, the noise being generated until the end of actuating the indicator device.

31 Claims, 17 Drawing Sheets

(51) Int. Cl.
*A61M 5/32* (2006.01)
*A61M 5/315* (2006.01)
(52) U.S. Cl.
CPC ......... *A61M 5/3287* (2013.01); *A61M 5/3146* (2013.01); *A61M 2005/206* (2013.01)

(56) References Cited

FOREIGN PATENT DOCUMENTS

| WO | 2013/078200 A1 | 5/2013 |
| WO | 2013/175140 A1 | 11/2013 |
| WO | 2013/175144 A1 | 11/2013 |

OTHER PUBLICATIONS

International Search Report of PCT/FR2016/051312 dated Aug. 11, 2016 [PCT/ISA/210].

* cited by examiner

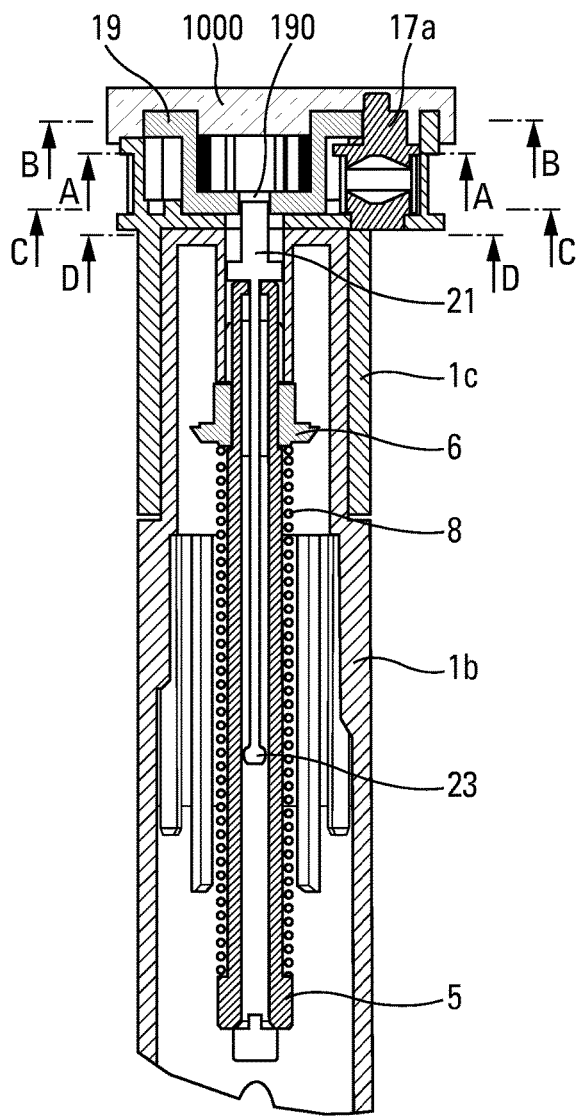
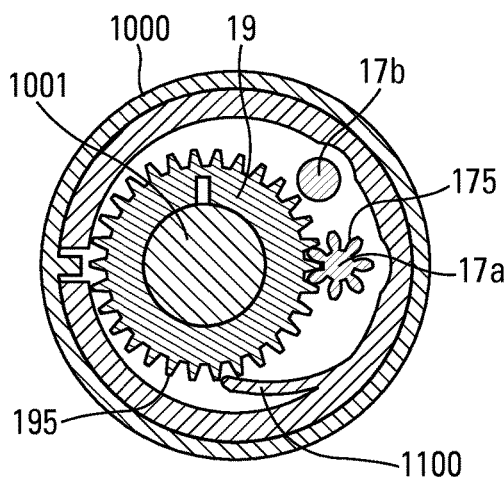
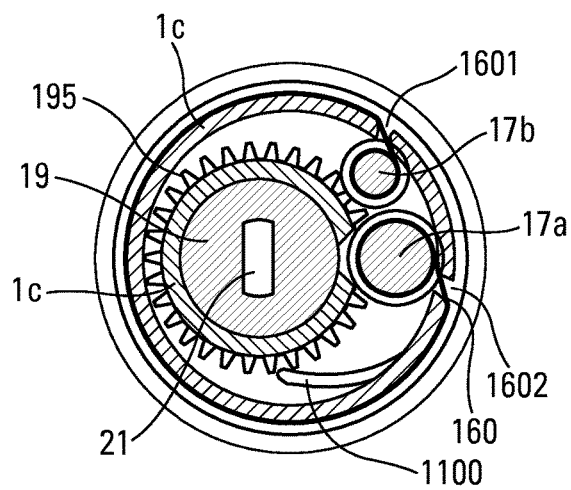
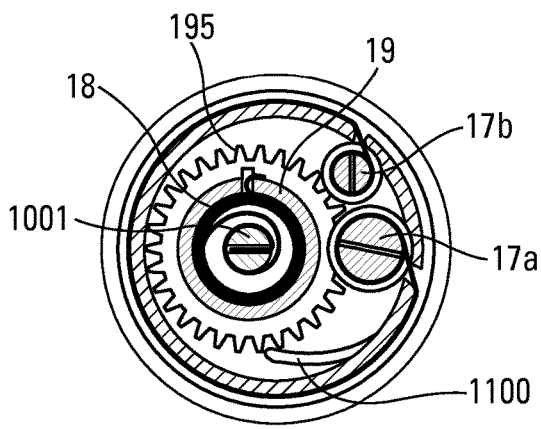
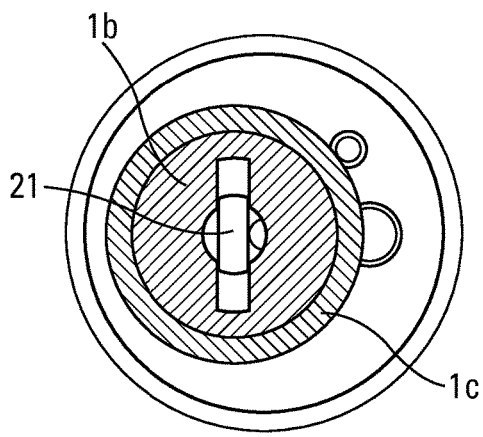
Fig. 11
Fig. 12b
Fig. 12c
Fig. 12a
Fig. 12d

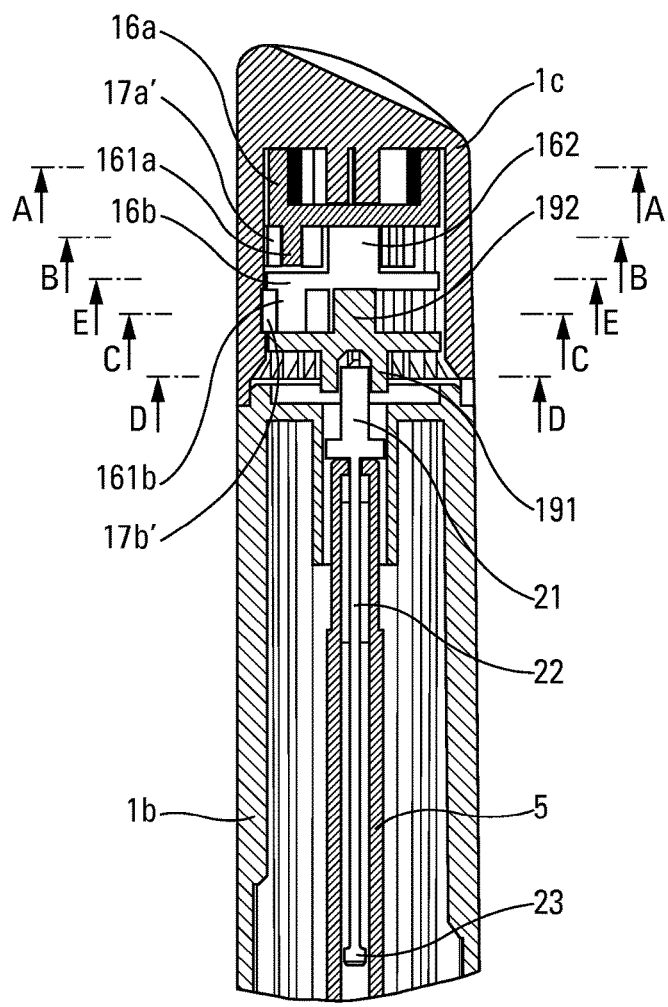
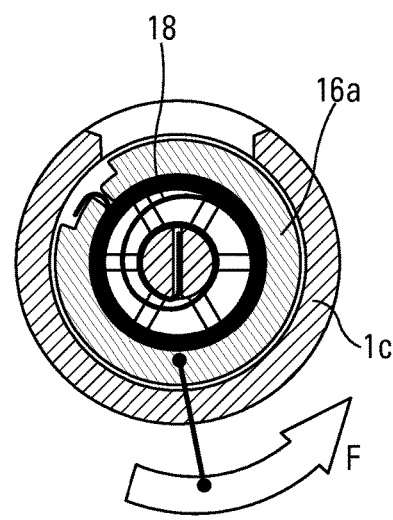
Fig. 15                                    Fig. 16a
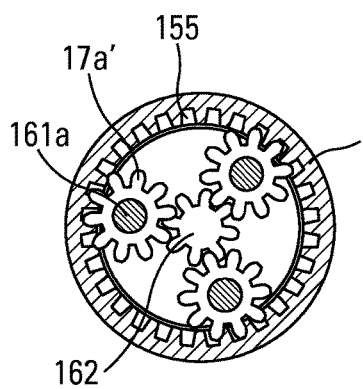 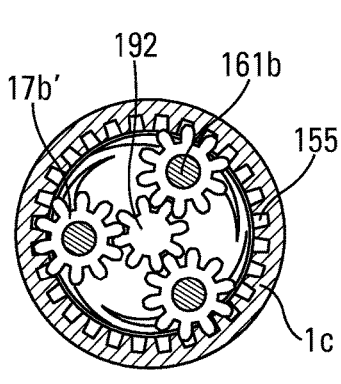 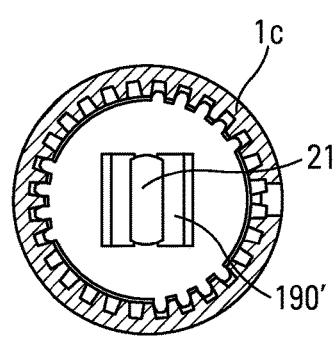
Fig. 16b            Fig. 16c            Fig. 16d

AUTO-INJECTOR

CROSS REFERENCE TO RELATED APPLICATIONS

This application is a National Stage of International Application No. PCT/FR2016/051312, filed Jun. 2, 2016, claiming priority based on French Patent Application No. 15 55166, filed Jun. 5, 2015, the contents of all of which are incorporated herein by reference in their entirety.

The present invention relates to an autoinjector.

Autoinjectors are well known in the prior art. The purpose of such devices is mainly to inject the contents of a syringe automatically into a patient's body. Various systems exist for making the penetration of the needle into the body of the patient and the injection of the fluid contained in the syringe automatic. Autoinjectors are relatively complex devices that must satisfy a certain number of constraint requirements in order to be reliable. The robustness of the device, its handling, and its ease of use for the user are also important elements. In addition, since most autoinjectors are for single use, the cost of manufacture and of assembly is also a factor that needs to be taken into account.

Numerous autoinjectors exist on the market, but they present a certain number of drawbacks.

Thus, in particular when the volume of fluid is relatively large and/or when the injected fluid is relatively viscous, it is desirable to enable the fluid to diffuse from the injection site for a few seconds after said injection. When the user removes the autoinjector immediately after the end of injection, a fraction of the fluid may escape from the user's body, and this reduces the effectiveness of the treatment. It is thus desirable to make provision for the user to continue to hold the autoinjector against the body for a few seconds after the end of injection. This aspect is generally resolved in existing autoinjectors by the operating instructions that ask the user to count silently a certain number of seconds prior to removing the device. This is unreliable and thus unsatisfactory, since the system depends on the user who, in some circumstances, may be disturbed or weakened by the injection action that has just been performed.

Documents WO 2013/175140, WO 2013/175144, WO 2013/078200, WO 2012/022810, and WO 2011/109205 describe prior-art autoinjectors.

An object of the present invention is to provide an autoinjector that does not have the above-mentioned drawbacks, and that makes it possible to satisfy the various major requirements and constraints for safe and reliable use of the autoinjector.

Another object of the present invention is to provide an autoinjector that is reliable in use, that enables the user to determine when the autoinjector must be removed or may be removed from the body after use, that is safe and that prevents any risk of injury, and that is simple and inexpensive to manufacture and to assemble.

The present invention thus provides an autoinjector comprising:
- a body receiving a reservoir, said reservoir containing fluid and including a piston, such as a pre-filled syringe;
- a piston rod that is adapted to co-operate with the piston of said reservoir, said piston rod being movable by an injection spring between a primed position and an injection position in which said piston rod has moved the piston of the reservoir so as to inject the fluid into an injection site; and
- an indicator device for indicating to the user that said autoinjector may be removed from said injection site;

said autoinjector including a retarding system so as to delay the end of actuating said indicator device relative to the end of injection, said indicator device generating a noise while it is being actuated, said noise being generated until the end of actuating said indicator device.

Advantageously, said indicator device and/or said retarding system include(s) a rotary element that is adapted to co-operate with said body so as to generate said noise.

In a first advantageous embodiment, said indicator device comprises a cap, the body, an indicator tape, an indicator spring, a drive wheel, a winder wheel, and an unwinder wheel.

Advantageously, said indicator spring is made in the form of a spiral spring that is fastened firstly to said drive wheel and secondly to said body.

Advantageously, said drive wheel includes a gear that co-operates with a gear of the winder wheel, such that turning said drive wheel causes said winder wheel to turn, which causes said indicator tape to be wound onto said winder wheel.

Advantageously, said locking key comprises a head, a longitudinal rod, and an endpiece that is adapted to co-operate with the piston rod.

Advantageously, prior to triggering the indicator device, the head of the locking key is in its blocking position in which it co-operates with a corresponding profile of the drive wheel, such that said drive wheel is prevented from turning relative to said body and to said cap by said locking key.

Advantageously, when the piston rod arrives towards its end-of-injection position, it co-operates with the endpiece of the locking key so as to pull said locking key axially downwards out from its blocking position, such that said drive wheel is thus no longer prevented from turning by said locking key.

Advantageously, said body includes at least one flexible tab that is adapted to co-operate with said drive wheel so as to generate a noise while said drive wheel is turning.

In a second advantageous embodiment, said retarding system comprises an epicyclic gear train having at least one stage, and advantageously two stages, said epicyclic gear train comprising a retarding spring, at least one planet carrier, each carrying at least one planet gear, a trigger, and a locking key so as to prevent said trigger from turning until the end of injection.

Advantageously, said retarding spring is made in the form of a spiral spring that is fastened firstly to a planet carrier or to the trigger and secondly to the body.

Advantageously, each planet gear of a planet carrier co-operates firstly with said body and secondly either with another planet carrier or with said trigger.

Advantageously, said body includes a ring gear on its inside surface, said ring gear co-operating with at least one planet gear.

Advantageously, said trigger includes a central pin that is provided with a sun gear that co-operates with at least one planet gear.

Advantageously, said epicyclic gear train comprises two planet carriers, each carrying three planet gears.

Advantageously, said locking key comprises a head, a longitudinal rod, and an endpiece that is adapted to co-operate with the piston rod.

Advantageously, prior to triggering the retarding system, the head of the locking key is in its blocking position in which it co-operates with a corresponding profile of the body and with a corresponding profile of the trigger, such that said trigger is prevented from turning relative to said body by said locking key.

Advantageously, when the piston rod arrives towards its end-of-injection position, it co-operates with the endpiece of the locking key so as to pull said locking key axially downwards out from its blocking position, such that said trigger is thus no longer prevented from turning by said locking key.

Advantageously, said trigger includes at least one flexible tab that is adapted to co-operate with said body so as to generate a noise while said trigger is turning.

In a third advantageous embodiment, said retarding system comprises a dashpot, a shear member arranged in said dashpot, and a fluid arranged in said dashpot around said shear member, one of said dashpot and of said shear member being rotatably mounted in said body, and the other one of said dashpot and of said shear member being stationary in rotation, the turning of one relative to the other being braked by shearing said fluid contained in said dashpot.

Advantageously, said dashpot is rotatably mounted in said body, and said shear member is stationary in rotation.

Advantageously, said dashpot includes projections on its inside surface, and said shear member includes projections on its outer surface, said projections generating impediments to the flow of the fluid.

Advantageously, said retarding system comprises said dashpot containing said fluid, said shear member, a retarding spring, a locking key, and said piston rod.

Advantageously, said locking key comprises a head, a longitudinal rod, and an endpiece that is adapted to co-operate with the piston rod.

Advantageously, prior to triggering the retarding system, the head of the locking key is in its blocking position in which it co-operates with a corresponding profile of the body and with a corresponding profile of said dashpot, such that said dashpot is prevented from turning relative to said body by said locking key.

Advantageously, when the piston rod arrives towards its end-of-injection position, it co-operates with the endpiece of the locking key so as to pull said locking key axially downwards out from its blocking position, such that said dashpot is thus no longer prevented from turning by said locking key.

Advantageously, said retarding spring is made in the form of a spiral spring that is fastened firstly to said dashpot or to said shear member and secondly to said body.

Advantageously, said dashpot includes at least one flexible tab that co-operates with a plurality of profiles of said body so as to generate a continuous noise while said retarding system is being actuated.

Advantageously, said autoinjector includes an actuator sleeve that includes a contact end for coming into contact with the user's body, said actuator sleeve extending inside said body at least in part, and being movable relative to said body between projecting positions in which said actuator sleeve projects out from said body at least in part, and an actuated position in which said actuator sleeve is moved axially into said body, said actuator sleeve being in a first projecting position before actuation of the autoinjector, and in a second projecting position after actuation of the autoinjector.

Advantageously, said reservoir includes a needle through which said fluid is injected into said injection site.

Advantageously, one of said rotary element and of said body includes at least one flexible tab that co-operates with adapted profiles that are formed on the other one of said rotary element and of said body so as to generate said noise.

Advantageously, the shapes and/or dimensions of said at least one flexible tab and/or of said adapted profiles vary so as to generate a noise that varies.

These characteristics and advantages and others of the present invention appear more clearly from the following detailed description, given by way of non-limiting examples, and with reference to the accompanying drawings, and in which:

FIG. 11 is a diagrammatic section view of a detail of a portion of the autoinjector in FIGS. 1 to 5, more particularly showing the FIG. 6 indicator device in the FIG. 1b position;

FIGS. 12a to 12d are diagrammatic section views, respectively on section planes A-A, B-B, C-C, and D-D in FIG. 11;

FIG. 15 is a diagrammatic section view of a detail of a portion of the autoinjector in FIGS. 13 and 14, more particularly showing the retarding system;

FIGS. 16a to 16d are diagrammatic section views, respectively on section planes A-A, B-B, C-C, and D-D in FIG. 15;

Figure 1A:
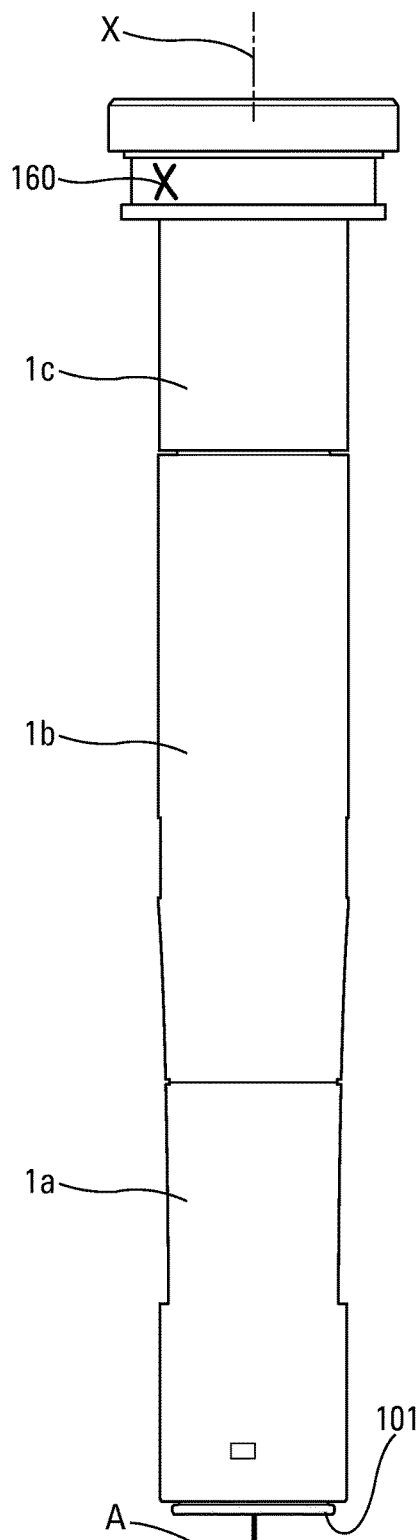
FIGS. 1a and 1b are diagrammatic views, respectively from the side and in section, of an autoinjector constituting a first advantageous embodiment of the present invention, in its after-pricking and before-injection position.

In the following description, the terms "top", "bottom", "high", and "low" refer to the positions shown in FIGS. 1a to 4, 11, 13a, 13b, 15, 20a, 20b, and 22. The terms "axial" and "radial" refer to the longitudinal central axis X, shown in particular in FIGS. 1a, 13a, and 20a, that corresponds to the longitudinal axis of the needle.

The autoinjector is described below with reference to three advantageous embodiments. It should nevertheless be observed that autoinjectors, which are complex appliances, comprise a plurality of modules for performing a plurality of functions. The various modules may be used separately and independently of one another, without necessarily being combined with the other modules, and in particular they could be used in autoinjectors of shape that is different from the shape shown in the drawings. Furthermore, it should be observed that the drawings are diagrammatic views, which do not necessarily represent the exact shape of the components of an autoinjector, and they are not necessarily to scale, in particular for purposes of clarity. In addition, the drawings do not necessarily represent all of the component elements of an autoinjector, but only the elements necessary for operation of the present invention. Thus, various additional and/or complementary elements and modules could be associated with the autoinjector shown in the figures.

The autoinjector shown in the figures comprises a body 1 in which an actuator sleeve 10 slides axially, the actuator sleeve 10 having a bottom end 101 that is for coming into contact with the body of the patient around the injection zone. In the embodiments, the autoinjector includes a lower body 1a, an intermediate body 1b, and an upper body 1c that are assembled together so as to form the body 1 of the autoinjector. Below, the term "body" and the numerical reference "1" are used to designate said unitary body formed by assembling said lower body 1a with said intermediate body 1b and said upper body 1c. It should be observed that the body 1 could be formed of any number of body portions, and that the embodiments in the figures, with three body portions, are not limiting.

A reservoir S may be inserted into said body 1 of the autoinjector, said reservoir S preferably being stationary in said body 1. The reservoir S contains fluid and includes a piston P and a needle A. The piston P is adapted to move in said reservoir S so as to inject the fluid through said needle A. Optionally, the present invention could also apply to a reservoir that does not have a needle, in particular in an injection device that does not have a needle.

The present description is made with reference to a syringe S that may be of any type. More generally, it is understood that the term "syringe" in the present description encompasses any type of reservoir associated with a needle. Preferably, the reservoir S is a pre-filled syringe.

Before the autoinjector is actuated, the needle A of the syringe S can be protected by a guard (not shown), the autoinjector possibly including a cap (not shown) that the user can remove before actuation. Removal of the cap advantageously causes the guard to be removed.

Before actuation, the actuator sleeve 10 is in a first projecting position in which it surrounds the needle A.

Figure 1B:
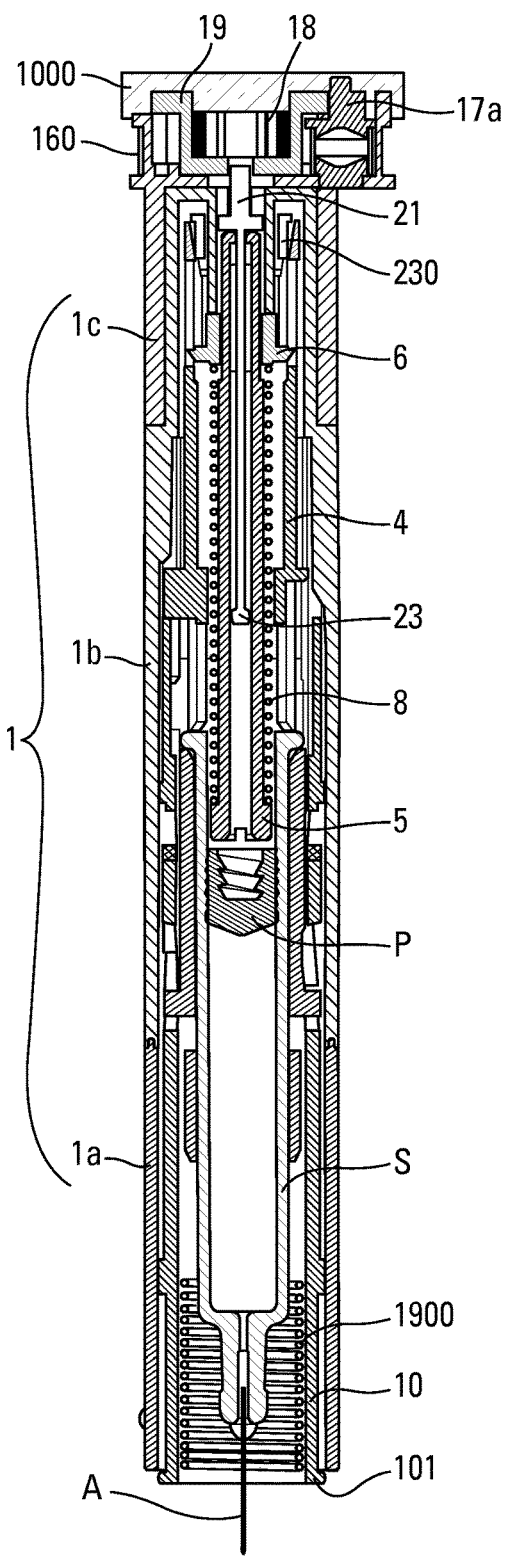
Figure 2A:
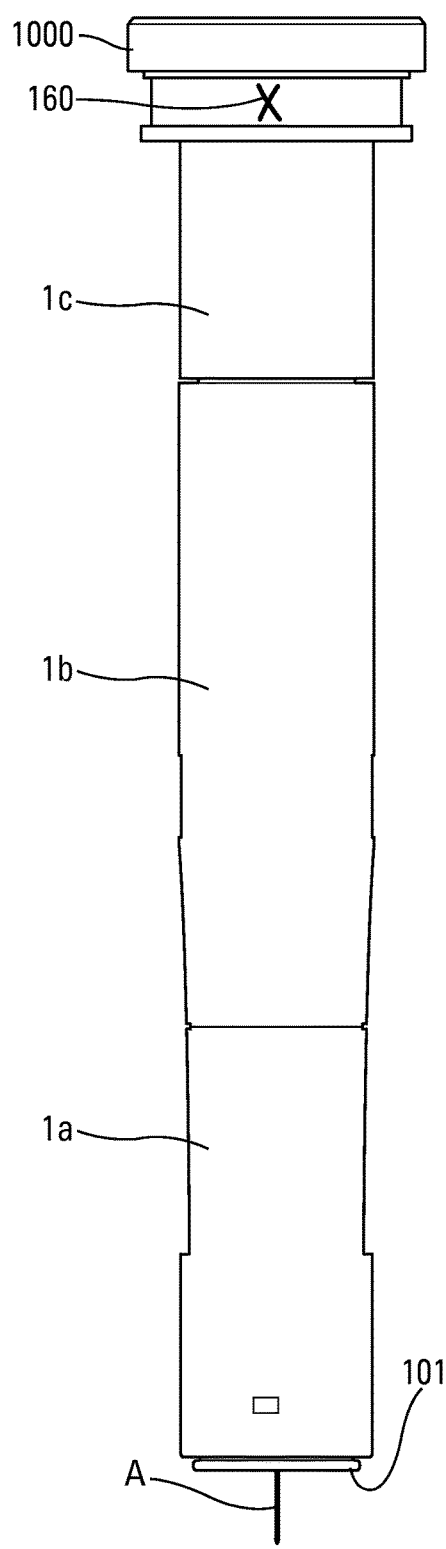
FIGS. 2a and 2b are views similar to the views in FIGS. 1a and 1b, after injection and while actuating the indicator device.
Figure 2B:
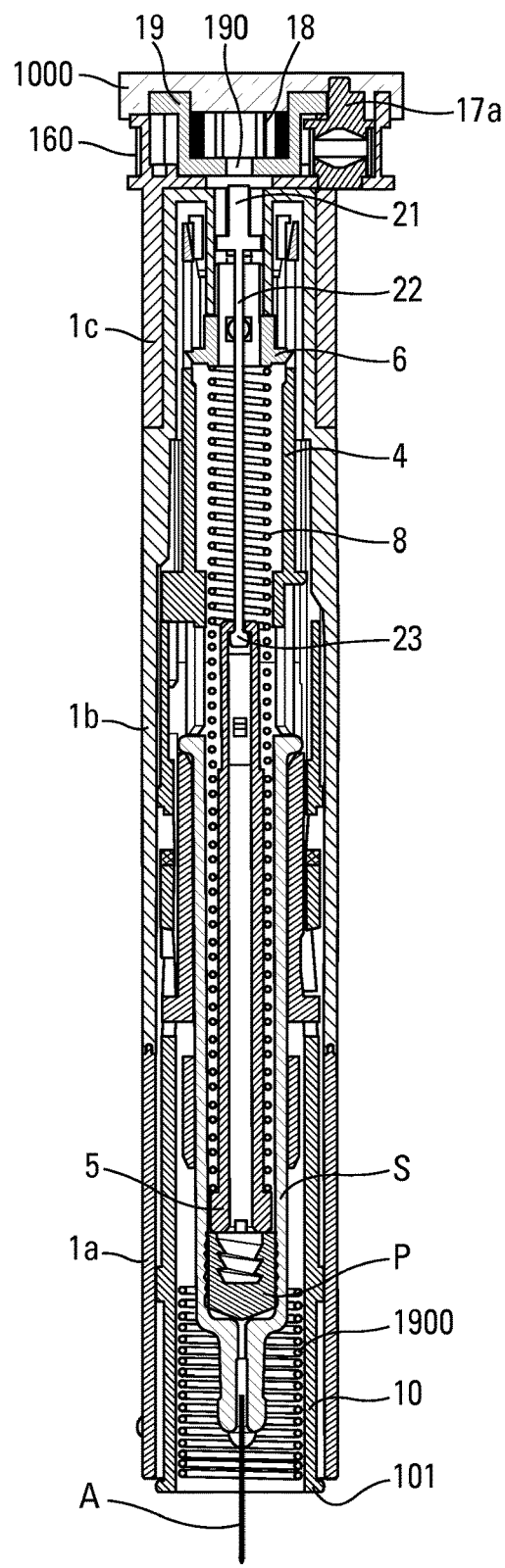
Figure 3A:
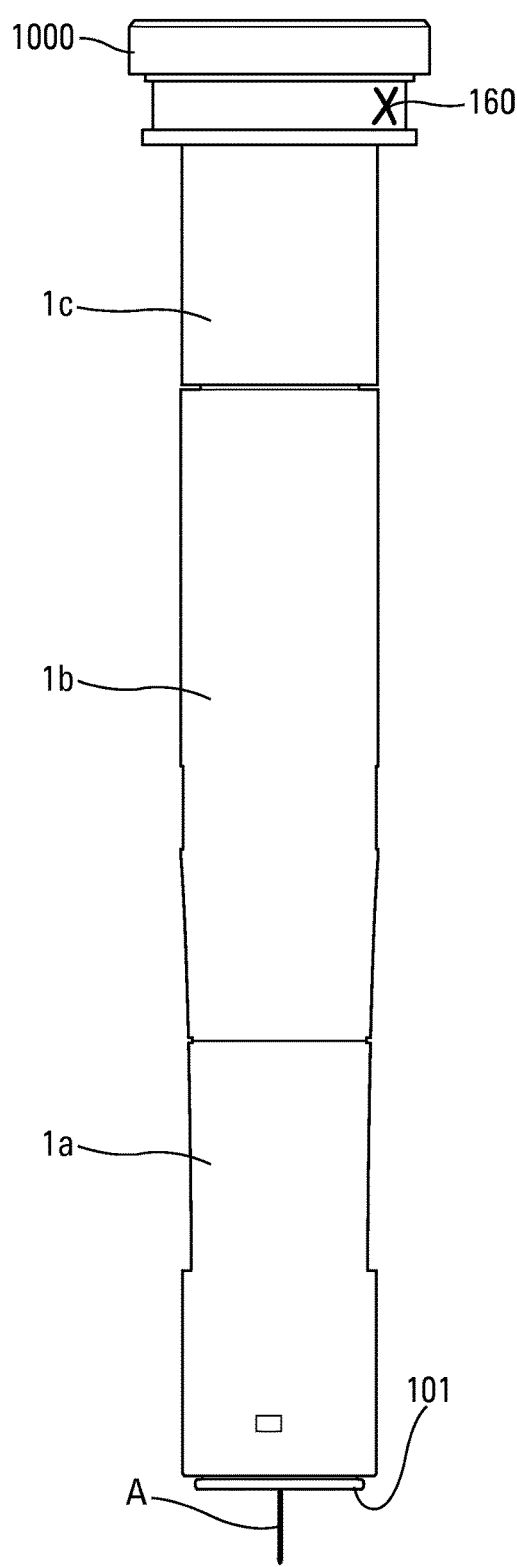
FIGS. 3a and 3b are views similar to the views in FIGS. 2a and 2b, at the end of actuating the indicator device.
Figure 3B:
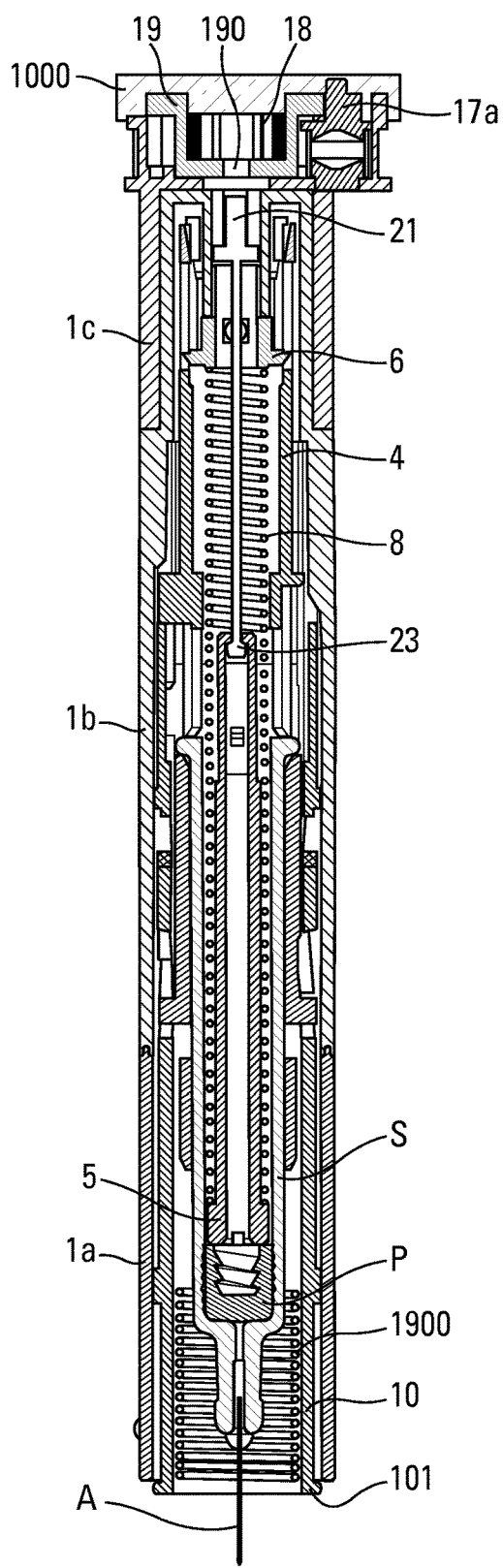

During actuation, the actuator sleeve 10 slides inside the body 1 towards an actuated position, so as to expose the needle A and enable pricking, and then injection of the fluid. FIG. 1b shows the autoinjector after pricking, but before injection. FIGS. 2b, 3b, 13b, and 20b show the autoinjector after injection.

Figure 4:
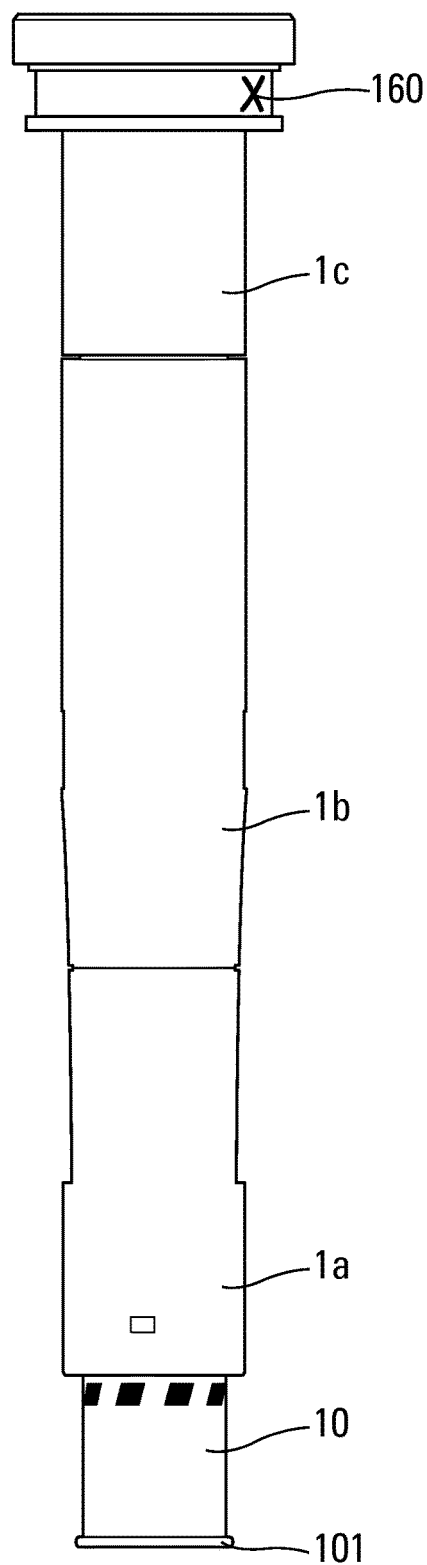
FIG. 4 is a view similar to the view in FIG. 3a, in the end-of-use position, after the autoinjector has been removed from the injection site.

After injection, when the user removes the autoinjector from the injection site, the actuator sleeve 10 returns into an end-of-use second projecting position in which it is once again arranged around the needle A, so as to avoid any risk of injury with said needle, as shown in FIG. 4.

The actuator sleeve 10 is advantageously urged towards its projecting positions by a resilient member or spring 190 that may be of any type. Advantageously, in said end-of-use position, said actuator sleeve 10 is locked, and can no longer be moved axially into said body 1. By way of example, locking may be achieved by tabs (not shown) that are secured to the body 1 or to the reservoir S, and that co-operate with openings (not shown) in said actuator sleeve 10 when said actuator sleeve reaches its second projecting position. Locking, that is not essential to the operation of the present invention, is not described in greater detail below. It could be achieved in ways that are different from the particular embodiment mentioned above. In particular, it could be achieved in accordance with the teaching of documents WO 2013/175140 or WO 2013/175142.

The autoinjector also includes an automatic injection system, in particular comprising a piston rod 5 that is adapted to co-operate with the piston P so as to move it in the reservoir S so as to dispense the fluid through the needle A. Conventionally, the piston rod 5 is urged by an injection spring 8 towards its dispensing position and, before actuation, it is held in its rest position by an appropriate injection lock. The injection spring 8 is shown only for the first and second embodiments.

An advantageous injection lock is described in particular in document WO 2015/155484.

The lock may comprises at least one blocking element (not shown) that is held in its blocking position by a blocking ring 230 that is fastened, in particular snap-fastened, on a support member 6 against which the injection spring 8 bears. Triggering said injection lock causes said injection means to be actuated, and thus fluid to be injected through the needle. Said injection lock may further include a control sleeve 4 that is arranged in said body 1, said control sleeve 4 containing said piston rod 5 and said injection spring 8, said piston rod 5 including a radial recess that receives at least one blocking element that is movable between a blocking position and an unblocking position. Said at least one blocking element is preferably of shape that is substantially spherical, such as a ball. Advantageously, said balls are urged radially outwards by said piston rod 5 and they are held in their blocking position by the blocking ring 230. The blocking ring 230 is axially movable relative to said piston rod 5 and relative to said support member 6 between a locking position in which it holds said balls in their blocking position, and an unlocking position in which said balls are released thereby unblocking said injection lock, enabling said injection spring 8 to move said piston rod 5 towards its injection position. In particular, the blocking ring 230 may be moved towards its unlocking position by said control sleeve 4.

When the needle A of the syringe S has penetrated the user's body, the blocking ring 230 is moved axially upwards, thereby causing the balls to be released from their blocking position, said balls then moving radially outwards. The piston rod 5 is then no longer held by the balls, and it is thus moved axially downwards so as to inject the fluid.

The autoinjector includes an indicator device for indicating to the user, in particular by an audible sound, by vibration, and/or by visual and/or tactile indication, that the autoinjector may be removed from the injection site. Said visual, audible, and/or tactile indicator device is preferably arranged at the rear end of said body 1, remote from said injection site. In particular, the present invention makes provision for generating a noise while actuating the indicator device, the end of said noise signifying the end of actuating the indicator device. Advantageously, in the embodiments shown, the indicator device further includes an indicator element that gives visual indication, by a suitable display 160 in one or more windows 11 of the body 1. Advantageously, tactile indication can also be provided.

FIGS. 1 to 12 show an indicator device of a first advantageous embodiment, FIGS. 13 to 19 show a second advantageous embodiment, and FIGS. 20 to 23 show a third advantageous embodiment.

In order to avoid the user removing the autoinjector from the injection site as soon as injection ends, the autoinjector includes a retarding system that delays the end of actuating said indicator device relative to the end of injection.

The main purpose of the indicator system is to generate audible indication for a predetermined period of time after the end of injecting the fluid into said body. In particular, the period of time enables the fluid to diffuse for a few seconds after it has been injected. Such an indicator system also provides a benefit for the user, who no longer has to count, e.g. up to 10, after being injected, where it is possible that the time taken to perform such counting might vary greatly from one user to another. With an indicator device associated with a retarding system, the sequence of using an autoinjector is facilitated.

Advantageously, the indicator device and/or the retarding system include(s) a rotary element that turns relative to the body, the continuous sound being generated during such turning, e.g. by means of one or more flexible tabs formed either on said rotary element or on said body, and co-operating with suitable profiles formed on the other of said rotary element and of said body.

Advantageously, it is possible to envisage modulating the sound produced by said tabs on said adapted profiles, for example:
by adjusting the shapes and/or the dimensions of the profiles; and/or
by using at least two tabs having shapes that are different. Thus, the sound produced could for example:
go from a low tone at the start, then to a high tone at the end, or vice versa; and/or
be multi-tone; and/or
have an intensity that varies during the delay.

The first embodiment in FIGS. 1 to 12 uses a flexible tape of the VHS cassette type for generating continuous audible indication, and advantageously corresponding visual indication. In a variant, the flexible tape could be replaced by a wire, or the like.

Figure 5:
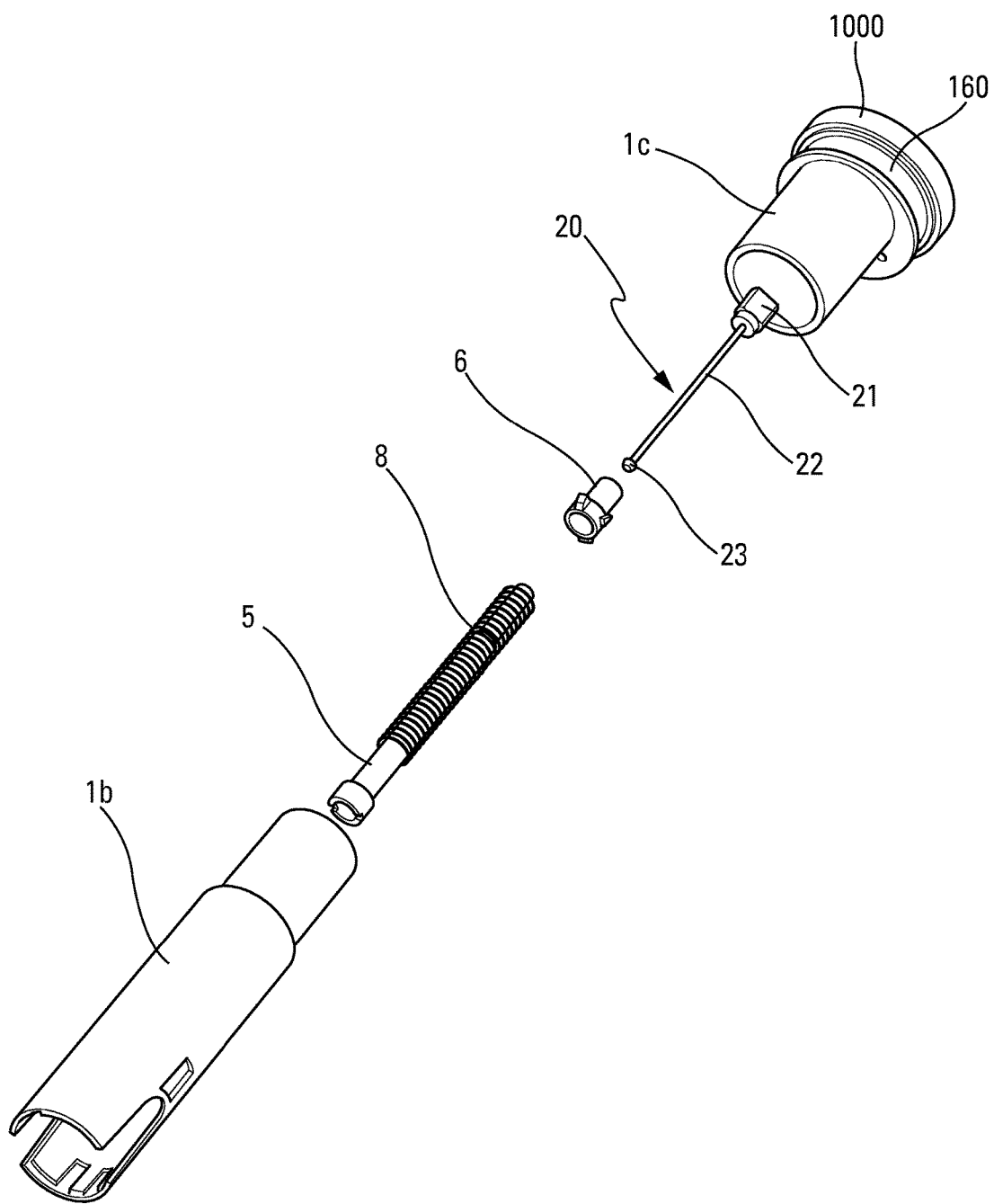
FIG. 5 is an exploded perspective view of a portion of the autoinjector constituting said first embodiment in FIGS. 1 to 4.

FIG. 5 is an exploded diagrammatic perspective view of the portion of the autoinjector that incorporates the indicator system of the first embodiment. The indicator system comprises an indicator module, a locking key 20, the injection spring 8, the piston rod 5, the support member 6, and the intermediate body 1b.

Figure 6:
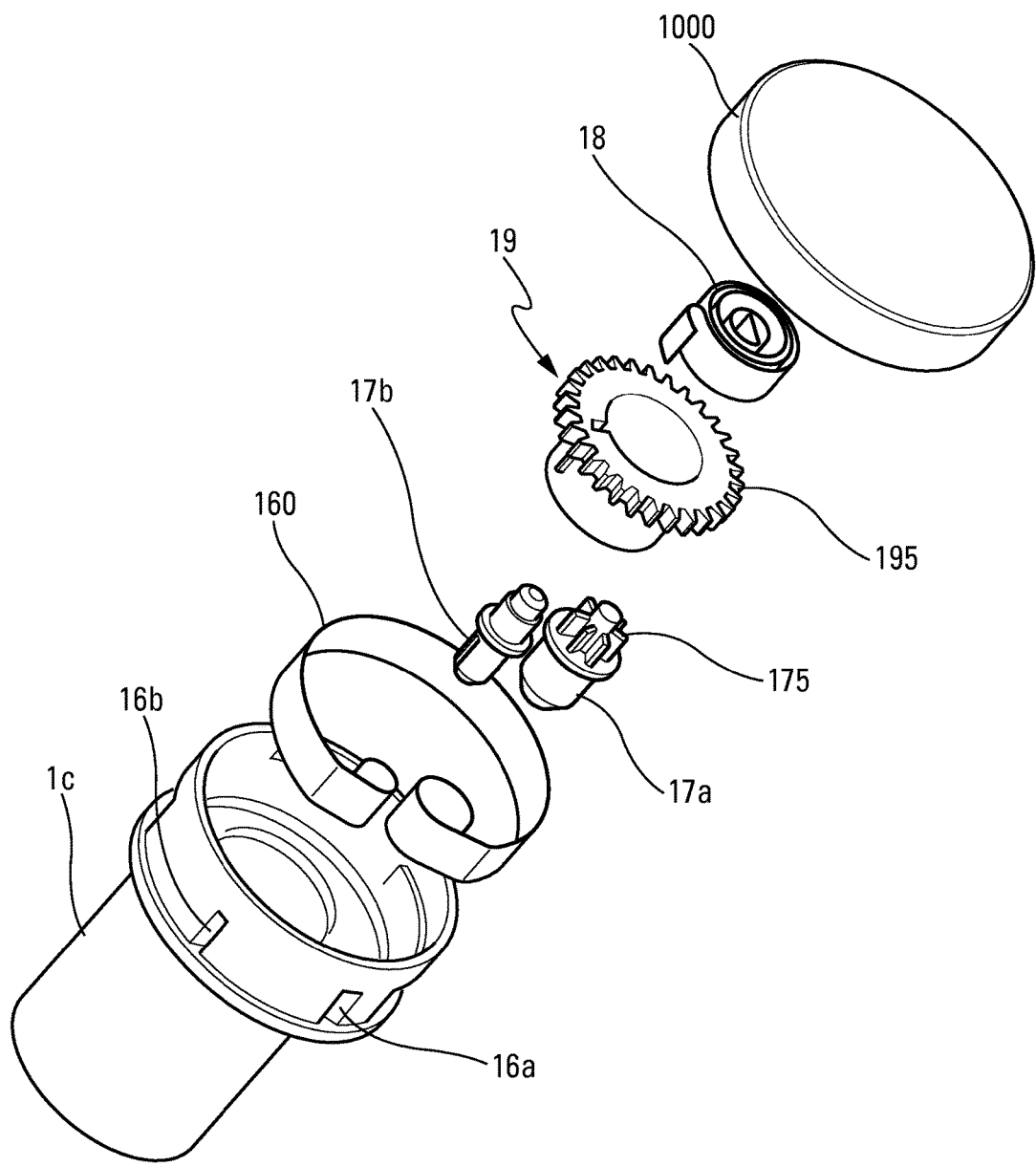
FIG. 6 is an exploded perspective view of the indicator device of said first embodiment in FIGS. 1 to 5.
Figure 7:
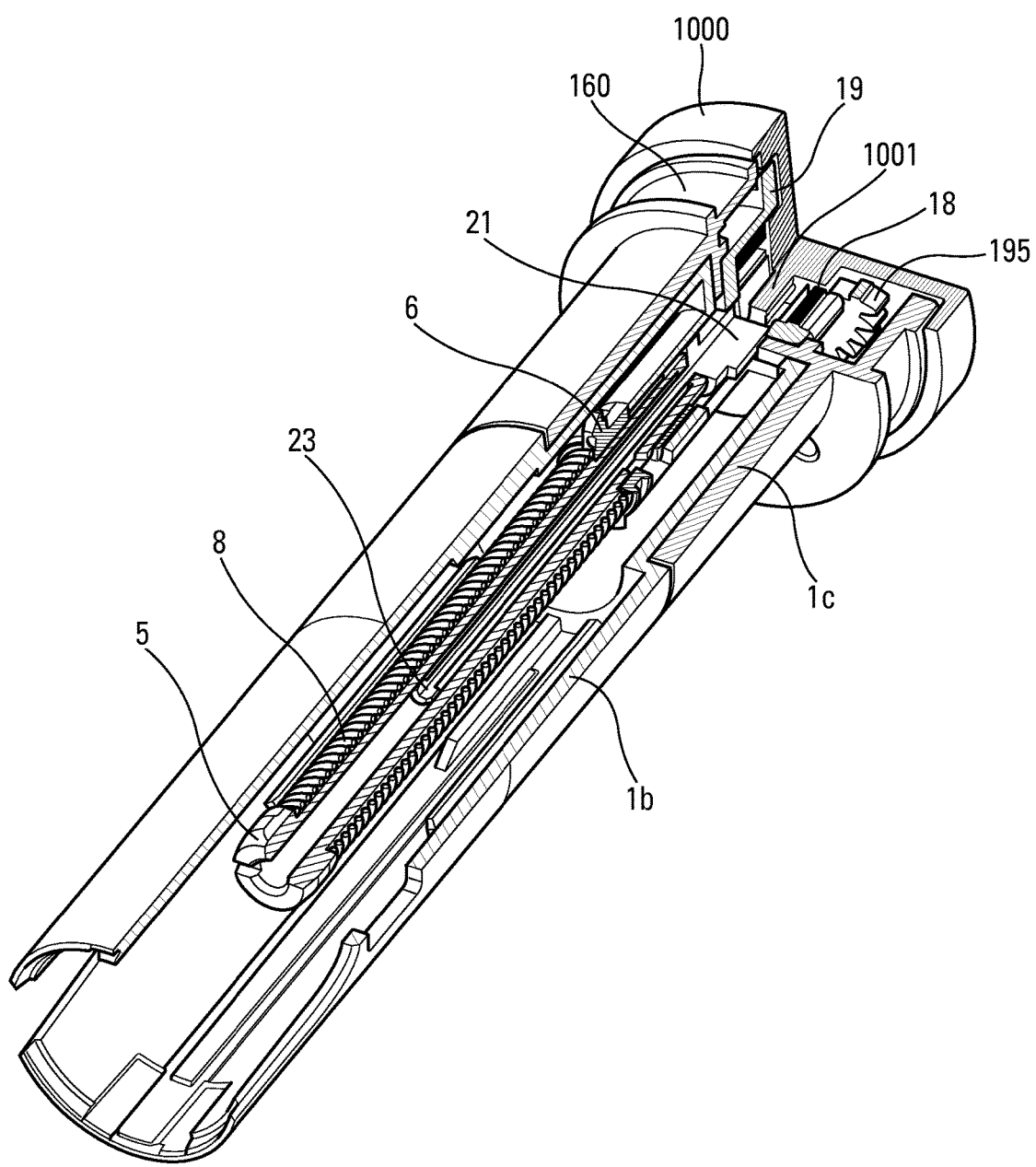
FIGS. 7 and 8 are cut-away perspective views of the FIG. 6 indicator device, respectively before and after the retarding system has been actuated.
Figure 8:
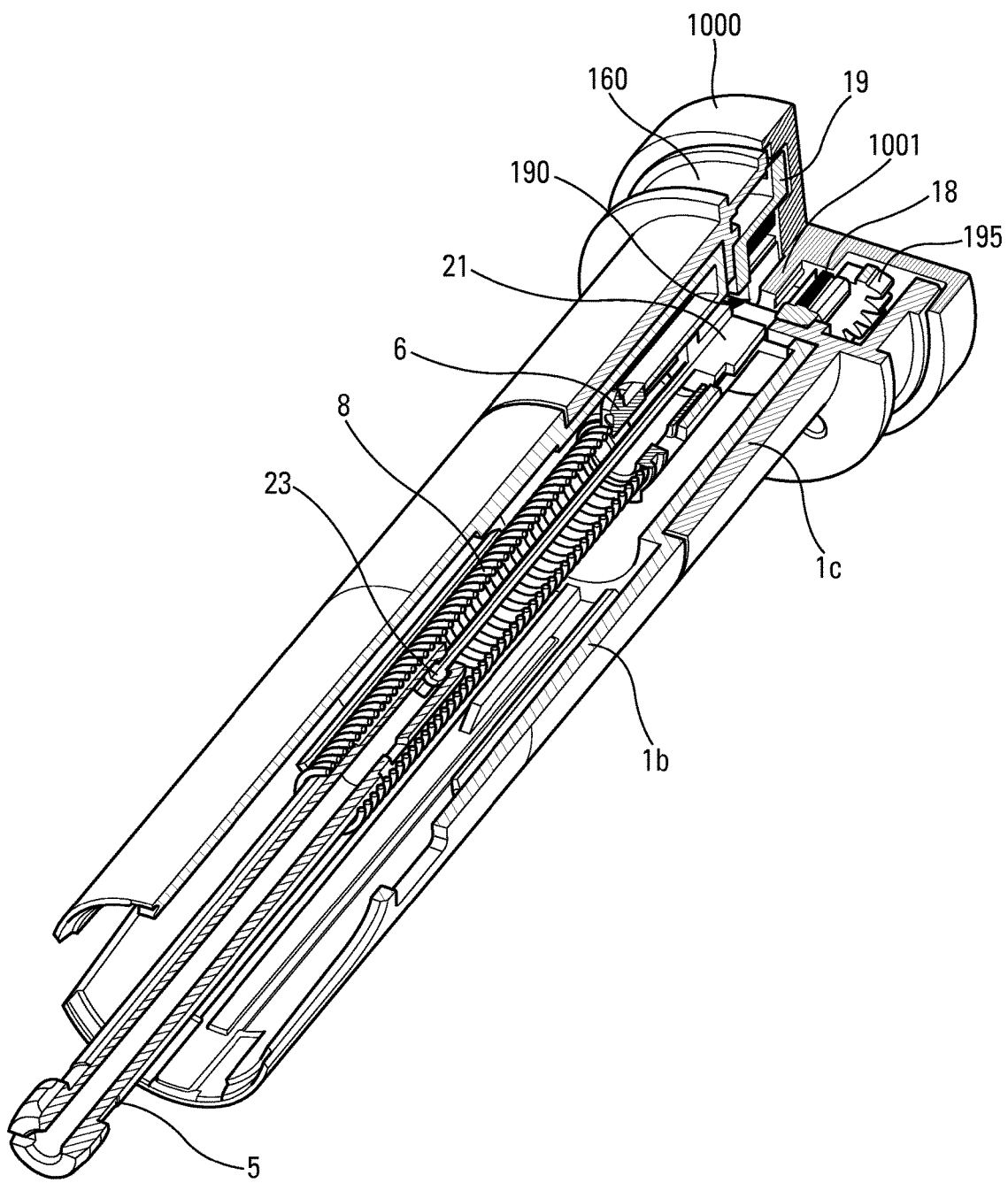
Figure 9:
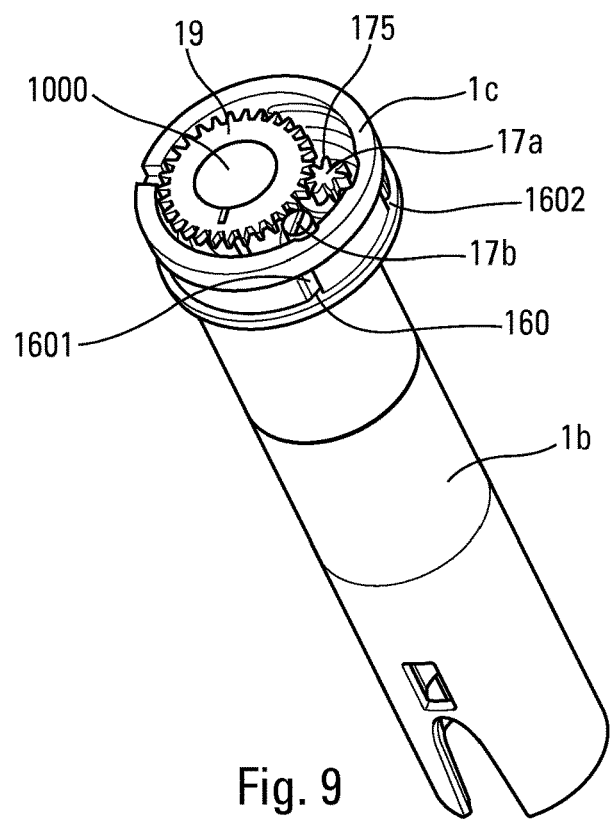
FIGS. 9 and 10 are perspective views, as seen from above, of a detail of the operation of the FIG. 6 indicator device.

FIG. 6 is an exploded diagrammatic perspective view of the FIG. 5 indicator module. The indicator module comprises a cap 1000, the upper body 1c, an indicator tape 160, an indicator spring 18, preferably made in the form of a spiral spring, a drive wheel 19, a winder wheel 17a, and an unwinder wheel 17b.

The drive wheel 19 includes a gear 195 that co-operates with a gear 175 of the winder wheel 17a. Advantageously, the unwinder wheel 17b turns freely under the effect of the traction exerted on it by the indicator tape 160, while said indicator tape is winding onto said winder wheel 17a.

Figure 10:
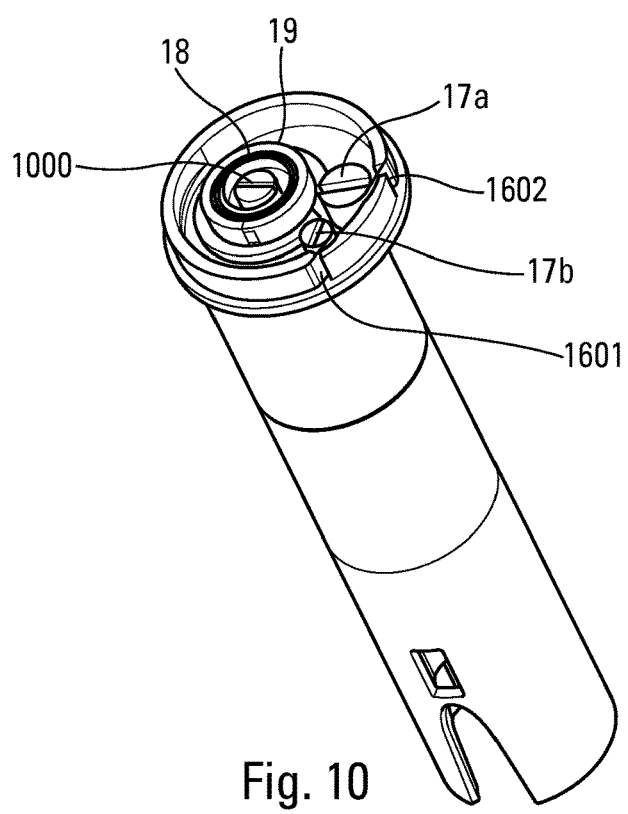
Figure 13A:
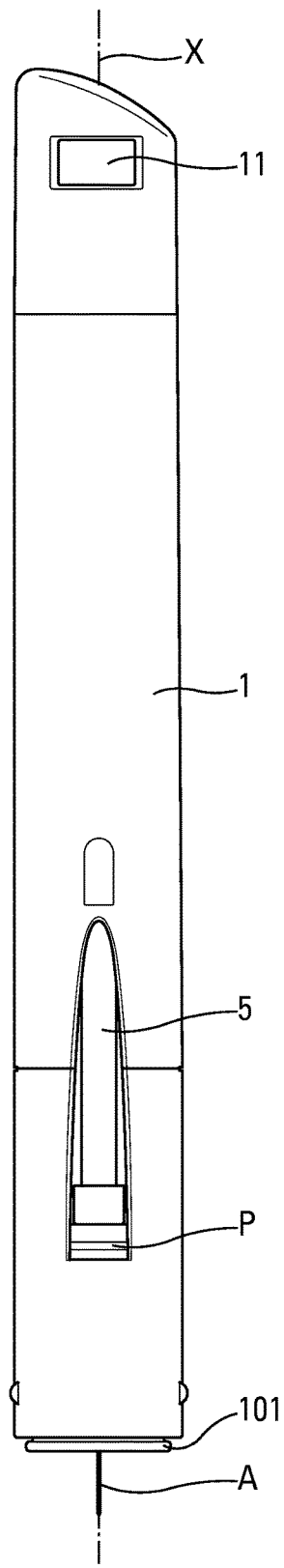
FIGS. 13a and 13b are diagrammatic views, respectively from the side and in section, of an autoinjector constituting a second advantageous embodiment of the present invention, in its after-injection position and at the start of actuating the retarding system.
Figure 13B:
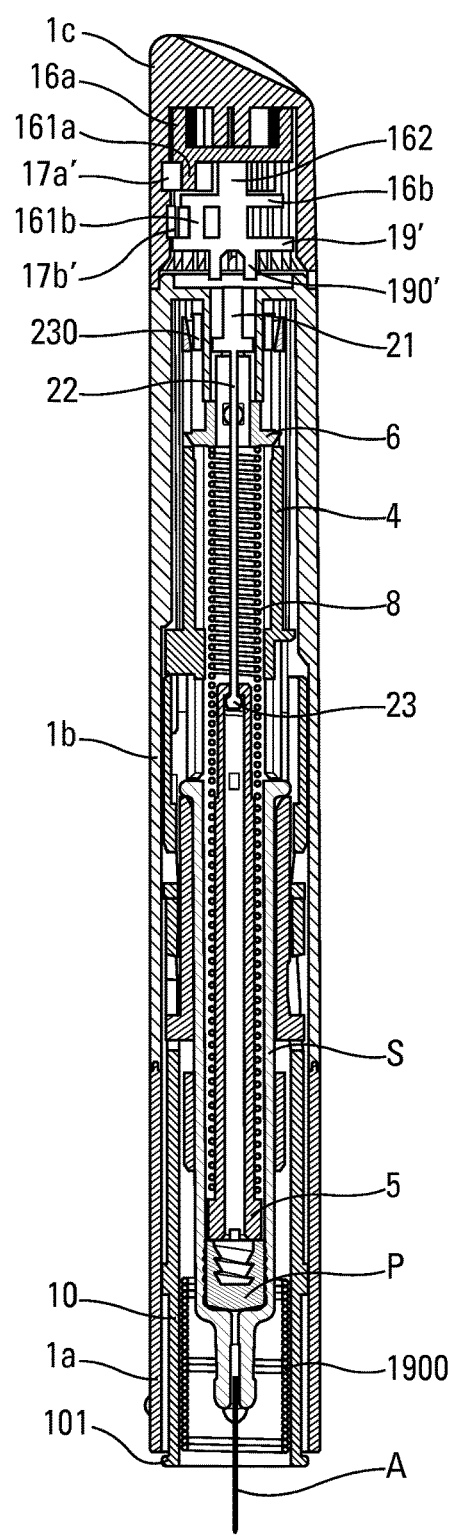

The spiral spring 18 is fastened firstly to the cap 1000, in particular on a central axial projection 1001 of said cap, and secondly to the drive wheel 19, as can be seen in particular in FIGS. 10 and 12a.

The indicator tape 160 is wound onto said unwinder wheel 17b, then extends through a first slot 1601 of the upper body 1c so as to go around said upper body 1c and pass via a second slot 1602 so as to be wound, finally, onto said winder wheel 17a.

The locking key 20 comprises a head 21 that is adapted to co-operate with the indicator module, a longitudinal rod 22, and an endpiece 23 that is adapted to co-operate with the piston rod 5.

In the position prior to triggering the indicator system, the head 21 of the locking key 20 is in its blocking position in which it co-operates with a corresponding profile 190 of the drive wheel 19, such that said drive wheel 19 is prevented from turning by said key. When the piston rod 5 arrives towards its end-of-injection position, it co-operates with the endpiece 23 of the locking key 20, and thus pulls said key 20 axially downwards. As a result, the head 21 of said locking key 20 moves axially out from said profile 190 of the drive wheel 19, such that said drive wheel 19 is no longer prevented from turning by said key 20.

The spiral spring 18 urges the drive wheel 19 to turn. While the drive wheel 19 is blocked by said locking key 20, the indicator device is thus also blocked.

When the indicator device is triggered, the spring 18 urges the drive wheel 19 to turn. The drive wheel turns the winder wheel 17a, which winds in the tape 160, and this simultaneously unwinds it from the unwinder wheel 17b.

While the drive wheel 19 is turning, at least one flexible tab 1100 of the body 1, in particular of the upper body 1c, co-operates with the gear 195 of the drive wheel 19 so as to generate a continuous sound. In a variant, the flexible tab 1100 could also co-operate with another portion of the drive wheel 19, or the drive wheel 19 could incorporate one or more flexible tabs that co-operate with profiles of the body 1. When the drive wheel 19 stops turning, the sound also stops, and the user knows that the autoinjector may be removed from the injection site.

Advantageously, the tape 160 includes markings, e.g. zones of color and/or signs or symbols, e.g. numbers, letters, or any other type of marking, so as to inform the user visually. In FIGS. 1a, 2a, 3a, and 4a, the marking is shown by an X, but this is only an example to illustrate the movement of the tape 160 while the indicator device is being actuated. The markings can be seen by the user on the outer portion of the upper body 1c, over which said indicator tape 160 extends between said first and second slots 1601, 1602. Optionally, the upper body could further include one or more windows that, by way of example, display the end of use in visual manner, in addition to the audible information provided by the cessation of said continuous noise. In a variant, the tape could include one or more holes or cut-outs that enable one or more markings formed on the body 1 to appear, before, during, and/or after winding in said tape.

The duration of indication and/or the delay of the end of indication relative to the end of injection can thus be predetermined by adjusting the parameters of the indicator device, and in particular the length of the indicator tape 160, the dimensions of the gears 195, 175 of the drive and winder wheels 19, 17a, the characteristics of the indicator spring 18, etc.

The second embodiment in FIGS. 13 to 19 makes use of an epicyclic gear train for generating said delay between the end of injection and the end of actuating the indicator device.

Figure 14:
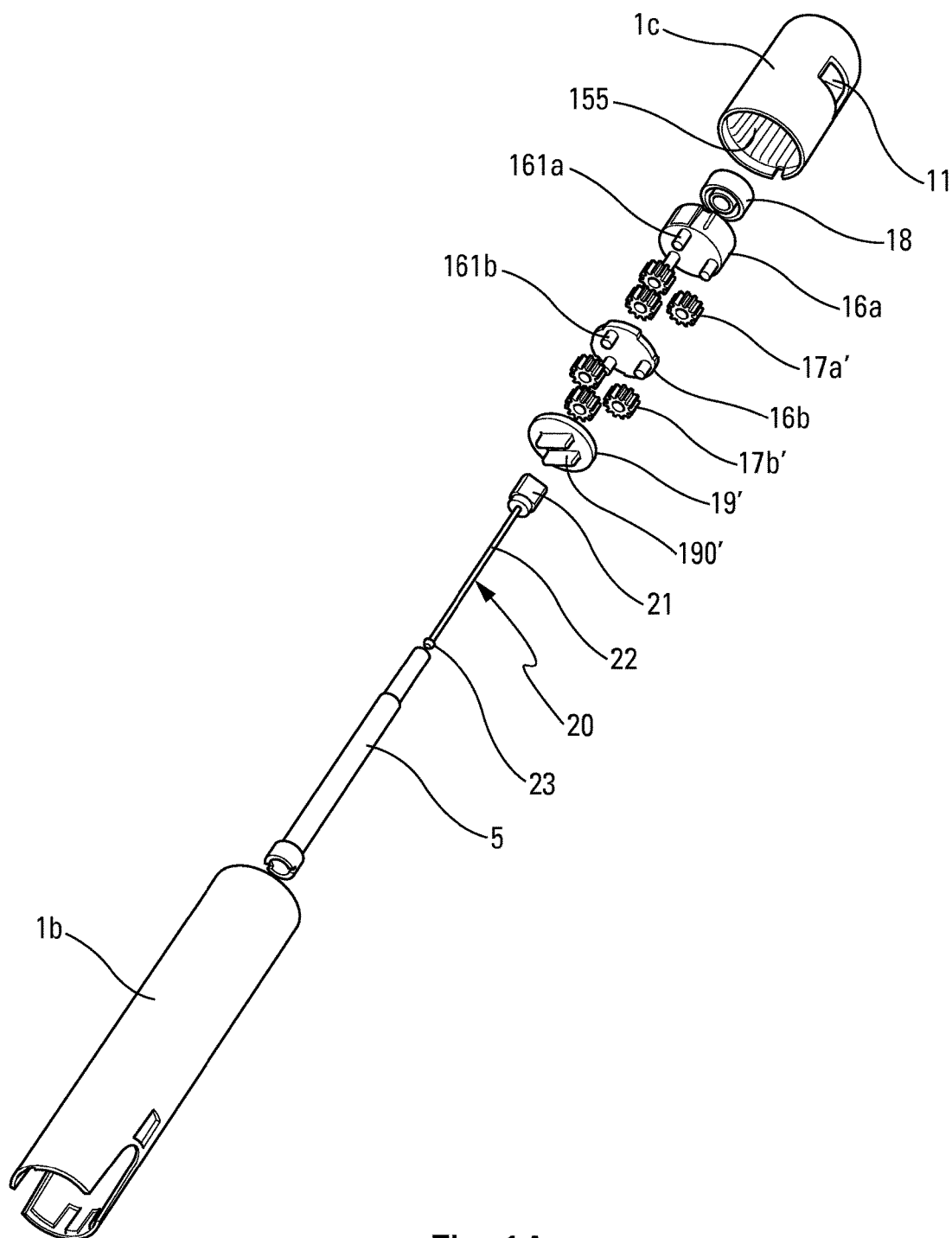
FIG. 14 is an exploded perspective view of the retarding system of said second embodiment in FIGS. 13a to 13b.

FIG. 14 is an exploded perspective view of the retarding system of the second embodiment. The retarding system comprises the upper body 1c, a retarding spring 18, preferably made in the form of a spiral spring, at least one planet carrier 16a, 16b, each carrying at least one planet gear 17a', 17b', a trigger 19', a locking key 20, the piston rod 5, and the intermediate body 1b.

Each planet carrier 16a, 16b associated with its planet gears 17a', 17b' forms a stage of the retarding system. In the embodiment shown in FIGS. 13 to 19, there are two stages stacked axially, with a first planet carrier 16a and a second planet carrier 16b, but any number of stages could be provided, e.g. a single stage or more than two stages.

The spiral spring 18 is fastened firstly to the first planet carrier 16a and secondly to the upper body 1c, as can be seen in FIG. 16a. In a variant, said spiral spring could be fastened to another planet carrier, e.g. the second planet carrier 16b in the embodiment shown, or to the trigger 19'. Furthermore, the spiral spring could be fastened to another portion of the body 1, e.g. the intermediate body 1b, or to any element that is fastened to said body 1.

In the embodiment shown, the first planet carrier 16a also forms a visual indicator element of the indicator device. In a variant, the indicator element could be formed by another planet carrier, e.g. the second planet carrier 16b in the embodiment shown, or by the trigger.

Each planet carrier 16a, 16b comprises a disk-shaped portion on which there are formed, on one side, one or more planet gear support pins 161a, 161b each receiving a planet gear 17a', 17b' in rotary manner. In the embodiment shown, there are three planet gears 17a', 17b' at each stage, such that there are three pins 161a, 161b on each planet carrier 16a, 16b. However, any number of planet gears is possible.

On the axial side remote from the support pins 161b, the second planet carrier 16b includes a central pin 162 that is provided with a sun gear, and that co-operates with the planet gears 17a' of the first planet carrier 16a.

Thus, the retarding system uses the principle of epicyclic gear trains. Each stage of the system makes it possible to decrease and/or slow down the turning of the preceding stage.

The locking key 20 comprises a head 21 that is adapted to co-operate with the retarding system, a longitudinal rod 22, and an endpiece 23 that is adapted to co-operate with the piston rod 5.

In the position prior to triggering the retarding system, the head 21 of the locking key 20 is in its blocking position in which it co-operates with a corresponding profile 12 of the intermediate body 1b and with a corresponding profile 190' of the trigger 19', such that said trigger is prevented from turning by said key. When the piston rod 5 comes towards its end-of-injection position, it co-operates with the endpiece 23 of the locking key 20, and thus pulls said locking key axially downwards. As a result, the head 21 of said locking key 20 moves axially out from said profile 190' of the trigger 19', such that said trigger 19' is no longer prevented from turning by said key 20.

On the axial side remote from said profile 190', the trigger includes a central pin 192 that is provided with a sun gear, and that co-operates with the planet gears 17b' of the second planet carrier 16b.

If there was only a single stage instead of the two shown, the second planet carrier 16b would not exist, and the planet gears 17a' of the first planet carrier 16a would co-operate directly with the central pin 192 of the trigger 19'. Likewise, if there were more than two stages, at least one additional planet carrier would exist between the second planet carrier 16b and the trigger 19'.

The upper body 1c includes a ring gear 155 on its inside surface, as can be seen clearly in FIGS. 16b and 16c. The ring gear 155 of the upper body 1c co-operates with the planet gears 17a', 17b' that are assembled on the planet carriers 16a, 16b.

The spiral spring 18 urges the first planet carrier to turn in the direction of arrow F in FIG. 16a. Such turning is transmitted via the planet gears 17a' to the central pin 162 of the second planet carrier 16b, and from there, via the planet gears 17b' to the central pin 192 of the trigger 19. While the trigger 19' is blocked by said locking key 20, the retarding system is thus also blocked.

When the retarding system is triggered, the spring 18 urges the first planet carrier 16a to turn. The planet gears 17a' are thus turned as a result of them meshing with the ring gear 155 of the upper body 1c. Such turning of the planet gears 17a' thus causes the central pin 162 of the second planet carrier 16b to turn, and the same operation is repeated with said second planet carrier 16b. The speed of turning of the first planet carrier 16a is thus lower than the speed of turning of said second planet carrier 16b. Each additional stage of the epicyclic gear train forming the retarding system further decreases the rate of turning, and thus further slows down the turning of the first planet carrier 16a. Thus, with two stages as shown in the figures, it is possible to keep the turning of the first planet carrier 16a down to a single turn, while the trigger 19' simultaneously performs about twenty revolutions.

Depending on the number of stages and/or depending on the number of planet gears and/or depending on the shape of the planet carriers and/or depending on the dimensions of the gears used, it is possible to adjust, quite accurately, the time between the moment at which the retarding system is triggered, at the end of injection, and the moment at which the first planet carrier 16a has performed its predefined turning so as to provide the indication, and in particular to indicate in the window of the indicator that the autoinjector may be removed from the injection site. The end of actuating the indicator device is thus delayed relative to the end of injection, thereby enabling the injected fluid to diffuse in the injection site during this period of delay.

The speed ratio may vary greatly, i.e. the system may be used to slow down the first planet carrier 16a (speed ratio greater than 1), or to slow down the trigger 19' (speed ratio less than 1), e.g. when it is the trigger that forms the indicator element of the indicator device.

As variants to the planet gears co-operating with the ring gear 155 of the upper body 1c, it is also possible to envisage different kinds of transmission, e.g. by friction.

In the invention, means are provided to generate a noise while said retarding system is being actuated.

Figure 17:
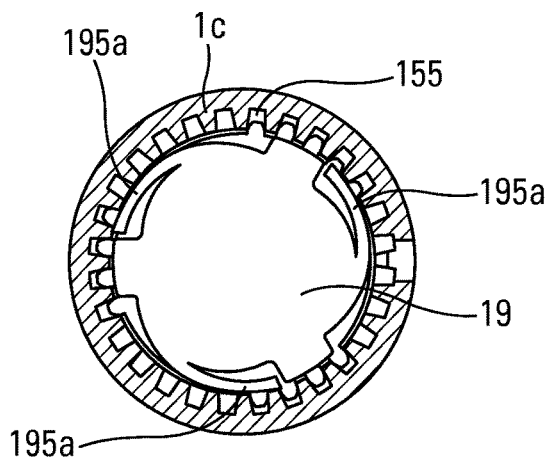
FIG. 17 is a diagrammatic section view on section plane E-E in FIG. 15, showing an advantageous variant embodiment.

FIG. 17 shows a trigger 19' including three flexible tabs 195a that slide over the ring gear 155 of the upper body 1c so as to generate a continuous noise while said trigger 19' is turning. This provides an audible indication that the retarding system is operating: when the noise stops, actuation of the retarding system has ended, and the user may remove the autoinjector from the injection site. Braking by friction can also be provided by the flexible tabs 195a.

Figure 18A:
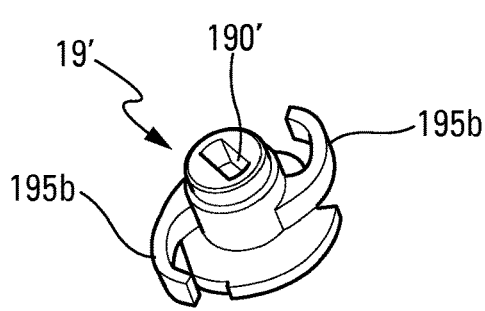
FIGS. 18a and 18b are perspective views of a detail of another variant embodiment.
Figure 18B:
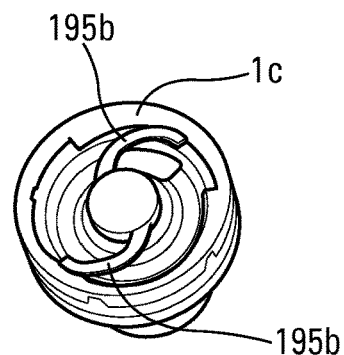

FIGS. 18a and 18b show another variant, in which the trigger 19' includes two flexible tabs 195b, with the ends of the tabs generating a noise throughout the entire time that said trigger 19' is turning, e.g. over an appropriate profile of the upper body. Naturally, and simultaneously, the tabs 195b can also brake the turning.

Figure 19:
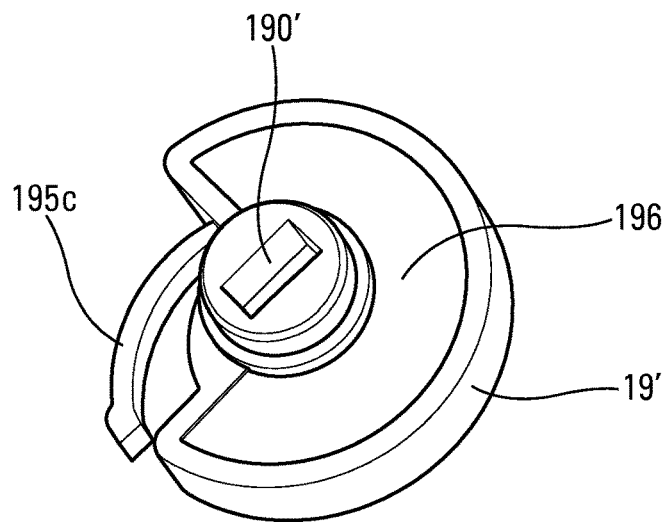
FIG. 19 is a perspective view of a detail of still another variant embodiment.
Figure 20A:
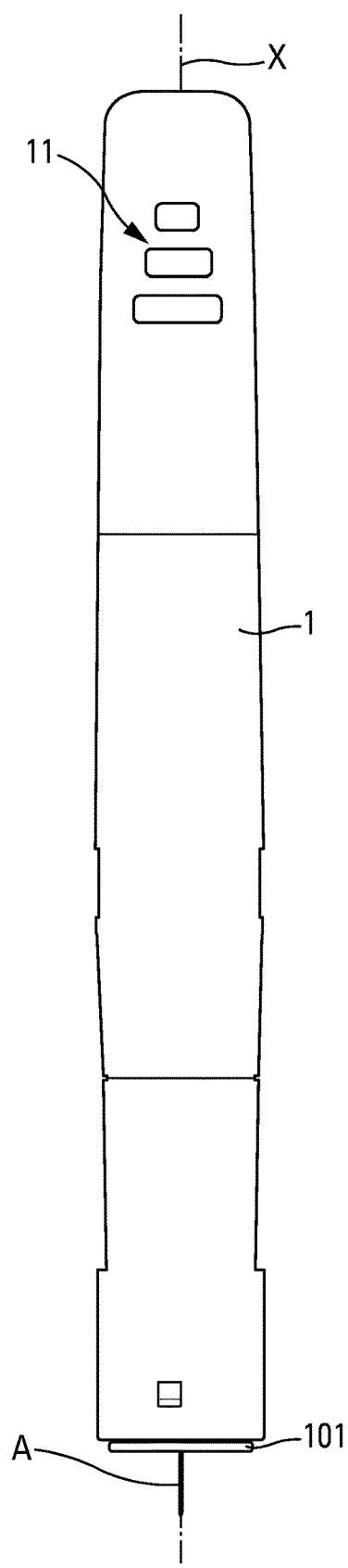
FIGS. 20a and 20b are diagrammatic views, respectively from the side and in section, of an autoinjector constituting a third advantageous embodiment of the present invention, in its after-injection position and at the start of actuating the retarding system.
Figure 20B:
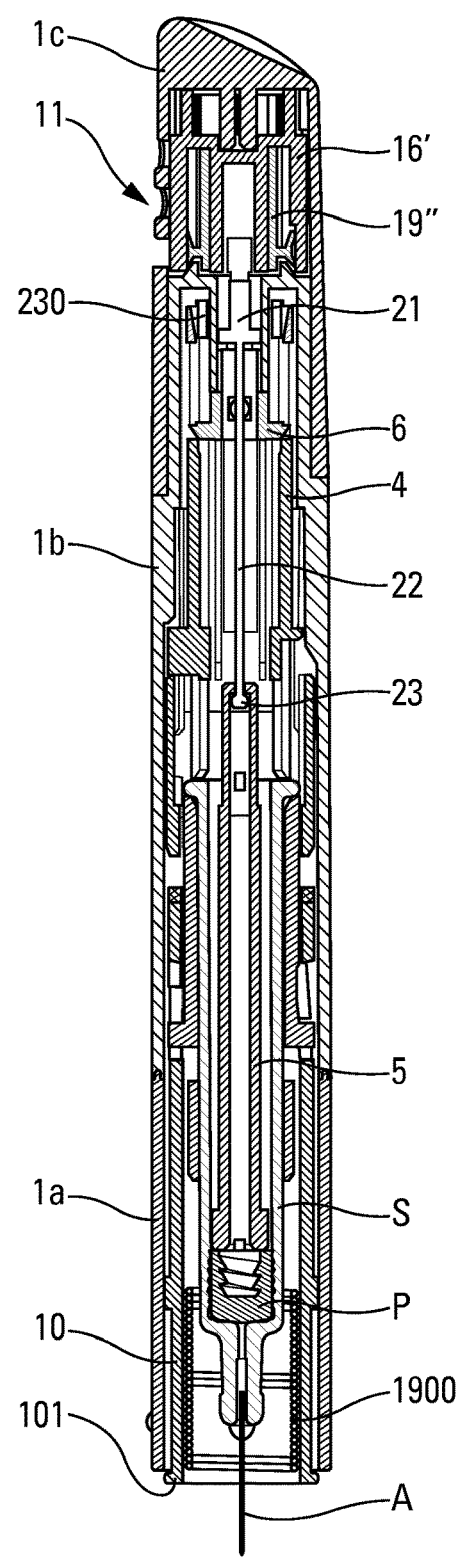

FIG. 19 shows still another variant, in which the trigger 19' includes a single flexible tab 195c that generates noise during turning, and that may also brake the turning. In this variant, the trigger 19' may include an inertial mass 196, that promotes braking.

Naturally the above-described flexible tab(s) 195a, 195b, 195c could also apply to a planet carrier 16a, 16b rather than to the trigger 19'.

The third embodiment in FIGS. 20 to 23 makes use of the phenomenon of fluid shear for generating said delay between the end of injection and the end of actuating the indicator device, and uses a dashpot 16', a shear member 19" arranged in said dashpot 16', and a fluid arranged in said dashpot 16', around said shear member 19".

In the embodiment shown, the shear member 19" does not turn relative to the body 1, and the dashpot 16' is movable in turning relative to said body 1. However, the inverse configuration can also be envisaged.

A fluid is arranged in said dashpot 16', around said shear member 19". Advantageously, the dashpot 16' includes projections 165 on its inside surface, and the shear member 19" includes projections 195 on its outer surface. The projections 165, 195 generate impediments to the flow of the fluid. Turning said dashpot 16' relative to said shear member 19" would thus shear the fluid, in particular when a projection 165 of the dashpot 16' faces a projection 195 of the shear member 19", as can be seen in FIG. 23b.

The term "fluid shear" designates a phenomenon of dynamic viscosity. Dynamic viscosity corresponds to the shear stress that accompanies the existence of a flow speed gradient in a fluid. When the viscosity increases, the ability of the fluid to flow decreases.

Use is also made of the boundary layer phenomenon, which is associated with dynamic viscosity. The boundary layer is the interface zone between a body and the surrounding fluid during relative movement between them, and is a consequence of the viscosity. When a fluid flows along a wall that is assumed to be stationary, speeds on the wall are zero, whereas at infinity (i.e. far from the obstacle) they are equal to the speed of the non-disturbed flow. The relationship expressing their variation depends on the viscosity of the fluid that leads to friction between the adjacent layers: the slowest layer tends to brake the fastest layer which, in turn, tends to accelerate it. In these conditions, a high viscosity evens out the speeds as much as possible. In contrast, when the fluid has little viscosity, the various layers are much more independent: the speed at infinity is maintained to within a short distance from the obstacle, and there is greater speed variation in the small thickness of the boundary layer.

Depending on the viscosity of the fluid contained in the dashpot 16' and/or depending on the shape and/or the dimensions of the profiles 165, 195 of the dashpot 16' and of the shear member 19", it is possible to adjust said braking quite accurately, and thus to adjust the time between the moment at which the retarding system is triggered, at the end of injection, and the moment at which the dashpot 16' has performed its predefined turning so as to provide the audible and visual indication, and in particular to generate a continuous noise while it is turning and, at the end of turning, to indicate in the window of the indicator that the autoinjector may be removed from the injection site. The end of actuating the indicator device is thus delayed relative to the end of injection, thereby enabling the injected fluid to diffuse in the injection site during this period of delay.

Figure 21:
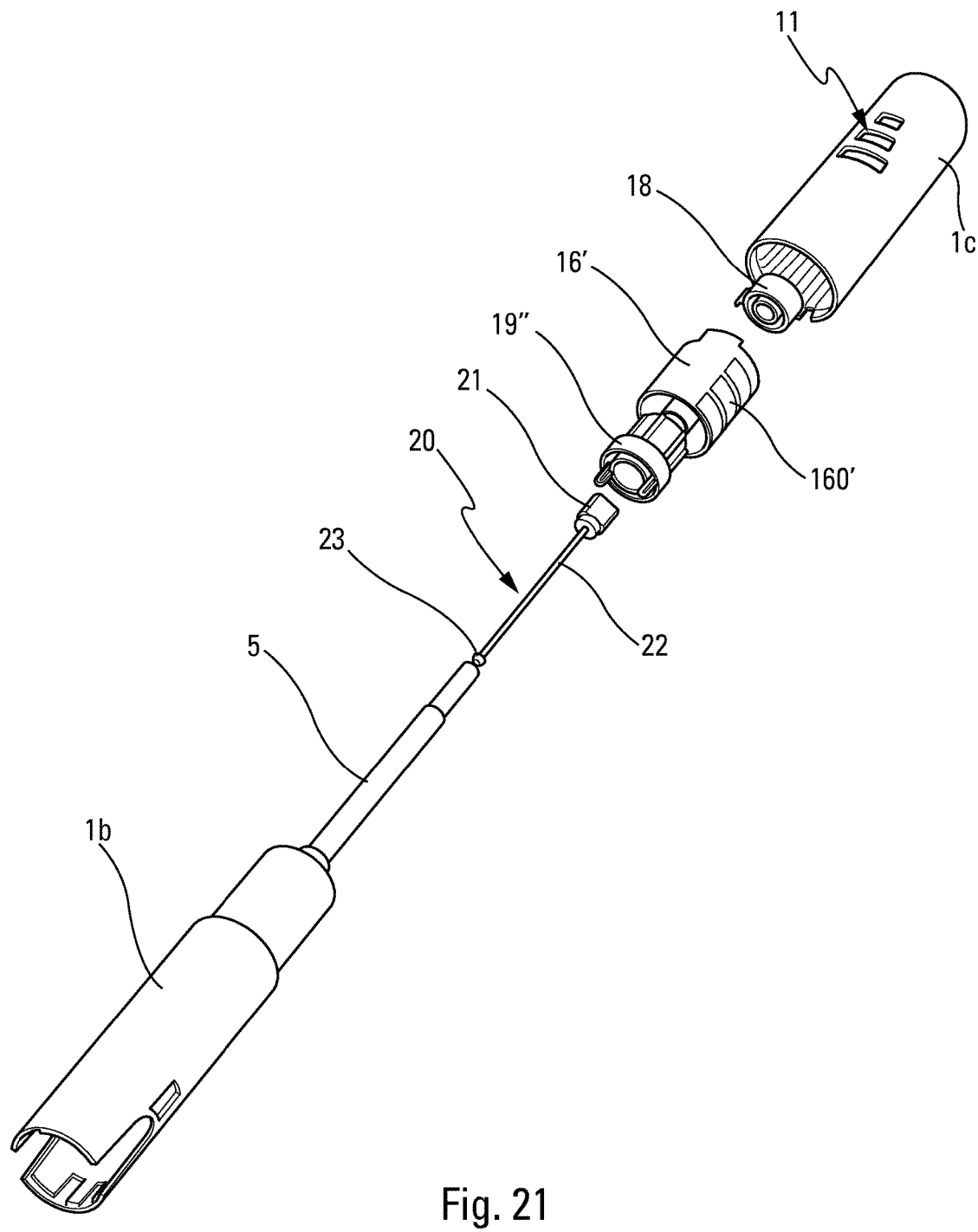
FIG. 21 is an exploded perspective view of the retarding system of said second embodiment in FIGS. 20a to 20b.
Figure 22:
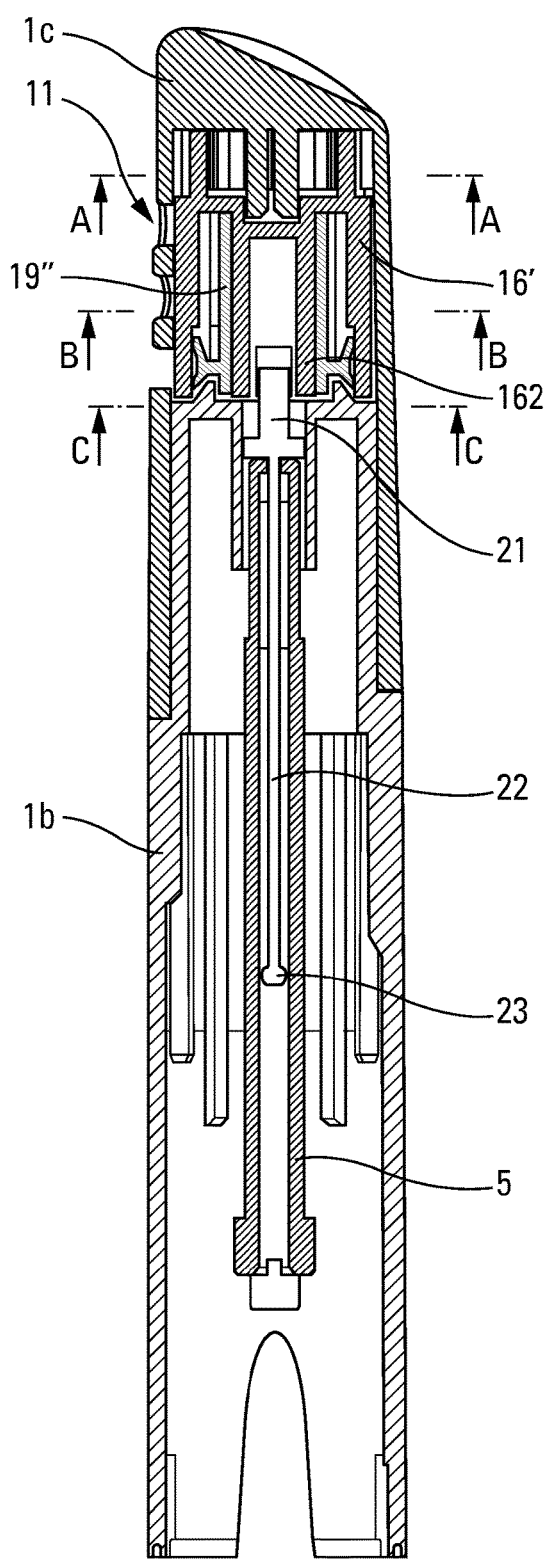
FIG. 22 is a diagrammatic section view of a detail of a portion of the autoinjector in FIGS. 20 and 21, more particularly showing the retarding system.

FIG. 21 is an exploded perspective view of the retarding system of the third embodiment. The retarding system comprises the upper body 1c, a retarding spring 18, preferably made in the form of a spiral spring, the dashpot 16' containing an appropriate fluid, the shear member 19" arranged in said dashpot 16', a locking key 20, the piston rod 5, and the intermediate body 1b.

In the embodiment shown, the dashpot 16' also forms a visual indicator element of the indicator device. Advantageously, said dashpot 16' may include an appropriate display 160' for indicating the end of use of the autoinjector in one or more windows of the body 1, in particular of the upper body 1c. In the embodiment shown in FIGS. 20 to 23, the body 1 includes three windows 11 that display the progress of the actuation of the retarding system. FIG. 21 shows the marking 160 made on the outside surface of said dashpot 16.

Figure 23A:
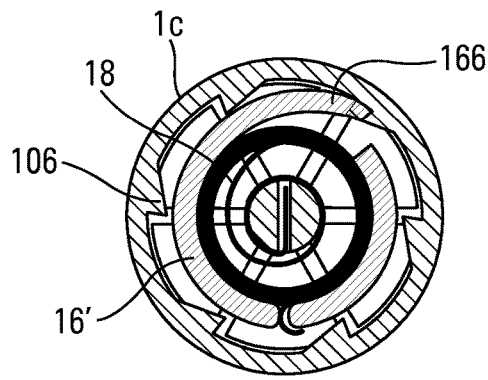
FIGS. 23a to 23c are diagrammatic section views, respectively on section planes A-A, B-B, and C-C in FIG. 22.
Figure 23B:
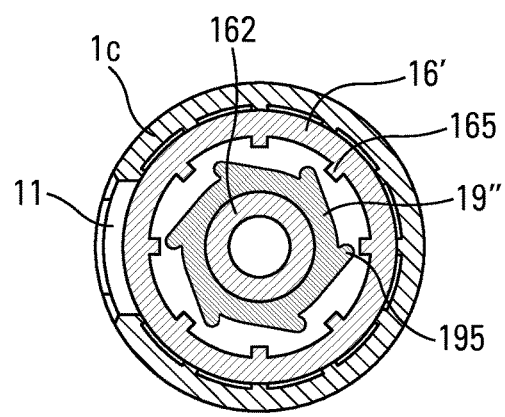
Figure 23C:
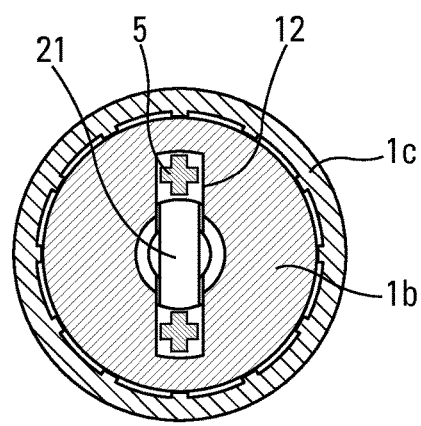

The spiral spring 18 is fastened firstly to the upper body 1c and secondly to the dashpot 16', as can be seen in particular in FIG. 23a. In a variant, the spiral spring could be fastened to another portion of the body 1, e.g. the intermediate body 1b, or to any element that is fastened to said body 1. In a variant, said spiral spring could be fastened to the shear member 19", in which event it is the dashpot 16' that does not turn relative to the body 1. In this variant, the rotary shear member could form the indicator element of the visual, audible, and/or tactile indicator device.

The locking key 20 comprises a head 21 that is adapted to co-operate with the retarding system, a longitudinal rod 22, and an endpiece 23 that is adapted to co-operate with the piston rod 5.

In the position prior to triggering the retarding system, the head 21 of the locking key 20 is in its blocking position in which it co-operates with a corresponding profile 12 of the intermediate body 1b and with a corresponding profile 161 of the dashpot 16', such that said dashpot is prevented from turning by said key. When the piston rod 5 comes towards its end-of-injection position, it co-operates with the endpiece 23 of the locking key 20, and thus pulls said locking key axially downwards. As a result, the head 21 of said locking key 20 moves axially out from said profile 161 of the dashpot 16', such that said dashpot 16' is no longer prevented from turning by said key 20. Advantageously, said profile 161 of the dashpot is formed on an inner sleeve 162 of the dashpot 16', which sleeve is arranged inside said shear member 19", as can be seen in particular in FIG. 22.

The spiral spring 18 urges the dashpot 16' to turn. While the dashpot 16' is blocked by said locking key 20, the retarding system is thus also blocked.

When the retarding system is triggered, the spring 18 urges the dashpot 16' to turn. The dashpot is subjected to a braking torque as a result of shearing the fluid contained between the wall of the dashpot 16' and the shear member 19". The turning of the dashpot 16' is thus braked by said fluid.

In the invention, the dashpot 16' includes at least one flexible tab 166, shown in FIG. 23a, having an end that generates a noise throughout the entire time that said dashpot 16' is turning, e.g. over appropriate profiles 106 of the upper body 1c, and thereby providing an audible indication that the retarding system is operating: when the noise stops, actuation of the retarding system and actuation of the indicator device have ended, and the user may remove the autoinjector from the injection site. Naturally, and simultaneously, the tab 166 can also further brake the turning. In a variant, a plurality of flexible tabs 166 could be provided, e.g. two tabs.

In the third embodiment described above, the fluid used in the retarding system may be of any appropriate type, e.g. grease.

A complete actuation stage of the autoinjector is described below, which stage applies to the three embodiments described above.

When the user wishes to use the autoinjector, the user takes hold of the device, e.g. at the body 1, and presses the actuator sleeve 10, which at rest, in its first projecting position, projects out from the lower body 1, against the part of the body where the injection is to be performed. The pressure exerted by the user on the actuator sleeve 10 causes said actuator sleeve to slide inside the body 1, thereby uncovering the needle and thus pricking the user as a result of the pressure exerted by the user on the autoinjector.

When the actuator sleeve 10 reaches its actuated position, which is its end position inside the body 1, it causes the injection stage to be triggered. It should be observed that the piston rod 5 slides inside the syringe A, pushing the piston P of said syringe under the effect of the injection spring 8. The fluid is thus dispensed.

At the end of injection, the indicator device is triggered, and the retarding system acts in such a manner that the indicator device is actuated completely only after a predetermined delay, generating a continuous noise between the end of injection and the end of actuating the indicator device.

After indicating the end of use, when the user may remove the autoinjector from the injection site, the actuator sleeve 10 once again moves out from the body 1 towards the end-of-use position, which is its second projecting position, under the effect of the spring of the actuator sleeve, with said actuator sleeve 10 being locked, and this guarantees absolute safety for the user and avoids any risk of injury with the needle after the device has been used.

In the embodiment shown, the first and second projecting positions of the actuator sleeve are different positions, however it should be observed that they could optionally be identical.

The present invention applies to devices used in particular for treatment of auto-immune diseases, e.g. of the rheumatoid arthritis, multiple scleroses, Crohn's disease type, for treatment of cancer, for antiviral treatments, e.g. of the hepatitis type, for treatment of diabetes, for treatment of anemia, or for treatment of allergy attacks, e.g. in the event of anaphylactic shock.

Although the present invention is described above with reference to several advantageous embodiments, naturally said embodiments are not limiting. In particular, the actuator sleeve and/or the injection lock and/or the retarding device and/or the indicator device could be made in some other way. Pricking by the needle and/or retracting the needle after injection could be controlled by one or more buttons. Other modifications can also be envisaged by the person skilled in the art, without going beyond the ambit of the present invention, as defined by the accompanying claims.

The invention claimed is:
1. An autoinjector comprising:
a body receiving a reservoir, said reservoir containing fluid and including a piston;
a piston rod that is adapted to co-operate with the piston of said reservoir, said piston rod being movable by an injection spring between a primed position and an injection position in which said piston rod has moved the piston of the reservoir so as to inject the fluid into an injection site; and
an indicator device for indicating to a user that said autoinjector may be removed from said injection site;
said autoinjector further comprising a retarding system so as to delay an end of actuating said indicator device relative to an end of injection, said indicator device generating a continuous noise while being actuated, said noise being generated until the end of actuating said indicator device, said indicator device and/or said retarding system including a rotary element with respect to said body, said continuous noise being generated during said rotation by one or more flexible tabs formed either on said rotary element or on said body, and cooperating with corresponding profiles formed on said rotary element when said one or more flexible tabs is formed on said body and on said body when said one or more flexible tabs is formed on said rotary element.

2. The autoinjector according to claim 1, wherein said indicator device comprises a cap, the body, an indicator tape, an indicator spring, a drive wheel, a winder wheel, and an unwinder wheel.

3. The autoinjector according to claim 2, wherein said indicator spring is made in a form of a spiral spring that is fastened firstly to said drive wheel and secondly to said cap.

4. The autoinjector according to claim 2, wherein said drive wheel includes a gear that co-operates with a gear of the winder wheel, such that turning said drive wheel causes said winder wheel to turn, which causes said indicator tape to be wound onto said winder wheel.

5. The autoinjector according to claim 2, wherein a locking key is provided, which comprises a head, a longitudinal rod, and an endpiece that is adapted to co-operate with the piston rod.

6. The autoinjector according to claim 5, wherein, prior to triggering the indicator device, the head of the locking key is in a blocking position in which the head of the locking key co-operates with a corresponding profile of the drive wheel, such that said drive wheel is prevented from turning relative to said body and to said cap by said locking key.

7. The autoinjector according to claim 6, wherein, when the piston rod arrives towards the end-of-injection position, the piston rod co-operates with the endpiece of the locking key so as to pull said locking key axially downwards out from the blocking position, such that said drive wheel is thus no longer prevented from turning by said locking key.

8. The autoinjector according to claim 2, wherein said body includes at least one flexible tab that is adapted to co-operate with said drive wheel so as to generate a noise while said drive wheel is turning.

9. The autoinjector according to claim 1, wherein said retarding system comprises an epicyclic gear train having at least one stage, and advantageously two stages, said epicyclic gear train comprising a retarding spring, at least one planet carrier, each carrying at least one planet gear, a trigger, and a locking key so as to prevent said trigger from turning until the end of injection.

10. The autoinjector according to claim 9, wherein said retarding spring is made in a form of a spiral spring that is fastened firstly to a planet carrier or to the trigger and secondly to the body.

11. The autoinjector according to claim 9, wherein each planet gear of a planet carrier co-operates firstly with said body and secondly either with another planet carrier or with said trigger.

12. The autoinjector according to claim 11, wherein said body includes a ring gear on an inside surface, said ring gear co-operating with at least one planet gear.

13. The autoinjector according to claim 11, wherein said trigger includes a central pin that is provided with a sun gear that co-operates with at least one planet gear.

14. The autoinjector according to claim 9, wherein said epicyclic gear train comprises two planet carriers, each carrying three planet gears.

15. The autoinjector according to claim 9, wherein said locking key comprises a head, a longitudinal rod, and an endpiece that is adapted to co-operate with the piston rod.

16. The autoinjector according to claim 15, wherein, prior to triggering the retarding system, the head of the locking key is in a blocking position in which the head of the locking key co-operates with a corresponding profile of the body and with a corresponding profile of the trigger, such that said trigger is prevented from turning relative to said body by said locking key.

17. The autoinjector according to claim 16, wherein when the piston rod arrives towards the end-of-injection position, the piston rod co-operates with the endpiece of the locking key so as to pull said locking key axially downwards out from the blocking position, such that said trigger is thus no longer prevented from turning by said locking key.

18. The autoinjector according to claim 9, wherein said trigger includes at least one flexible tab that is adapted to co-operate with said body so as to generate a noise while said trigger is turning.

19. The autoinjector according to claim 1, wherein said retarding system comprises a dashpot, a shear member arranged in said dashpot, and a fluid arranged in said dashpot around said shear member, one of said dashpot and of said shear member being rotatably mounted in said body, and the other one of said dashpot and of said shear member being stationary in rotation, a turning of one relative to the other being braked by shearing said fluid contained in said dashpot.

20. The autoinjector according to claim 19, wherein said dashpot is rotatably mounted in said body, and said shear member is stationary in rotation.

21. The autoinjector according to claim 19, wherein said dashpot includes projections on an inside surface of said dashpot, and said shear member includes projections on an outer surface of said shear member, said projections generating impediments to flow of the fluid.

22. The autoinjector according to claim 19, wherein said retarding system comprises said dashpot containing said fluid, said shear member, a retarding spring, a locking key, and said piston rod.

23. The autoinjector according to claim 22, wherein said locking key comprises a head, a longitudinal rod, and an endpiece that is adapted to co-operate with the piston rod.

24. The autoinjector according to claim 23, wherein, prior to triggering the retarding system, the head of the locking key is in a blocking position in which the head of the locking ring co-operates with a corresponding profile of the body and with a corresponding profile of said dashpot, such that said dashpot is prevented from turning relative to said body by said locking key.

25. The autoinjector according to claim 24, wherein, when the piston rod arrives towards the end-of-injection position, the piston rod co-operates with the endpiece of the locking key so as to pull said locking key axially downwards out from the blocking position, such that said dashpot is thus no longer prevented from turning by said locking key.

26. The autoinjector according to claim 22, wherein said retarding spring is made in a form of a spiral spring that is fastened firstly to said dashpot or to said shear member and secondly to said body.

27. The autoinjector according to claim 26, wherein said dashpot includes at least one flexible tab that co-operates with a plurality of profiles of said body so as to generate a continuous noise while said retarding system is being actuated.

28. The autoinjector according to claim 1, wherein said autoinjector includes an actuator sleeve that includes a contact end for coming into contact with the user's body, said actuator sleeve extending inside said body at least in part, and being movable relative to said body between projecting positions in which said actuator sleeve projects out from said body at least in part, and an actuated position in which said actuator sleeve is moved axially into said body, said actuator sleeve being in a first projecting position before actuation of the autoinjector, and in a second projecting position after actuation of the autoinjector.

29. The autoinjector according to claim 1, wherein said reservoir includes a needle through which said fluid is injected into said injection site.

30. The autoinjector according to claim 1, wherein one of said rotary element and of said body includes at least one flexible tab that co-operates with adapted profiles that are formed on the other one of said rotary element and of said body so as to generate said noise.

31. The autoinjector according to claim 30, wherein shapes and/or dimensions of said at least one flexible tab and/or of said adapted profiles vary so as to generate a noise that varies.

* * * * *